United States Patent
Brudniok

(10) Patent No.: US 9,730,757 B2
(45) Date of Patent: Aug. 15, 2017

(54) SURGICAL INSTRUMENT

(75) Inventor: Sven Brudniok, Augsburg (DE)

(73) Assignee: KUKA Roboter GmbH, Augsburg (DE)

( * ) Notice: Subject to any disclaimer, the term of this patent is extended or adjusted under 35 U.S.C. 154(b) by 140 days.

(21) Appl. No.: 13/985,466

(22) PCT Filed: Feb. 17, 2012

(86) PCT No.: PCT/EP2012/000719
§ 371 (c)(1),
(2), (4) Date: Aug. 14, 2013

(87) PCT Pub. No.: WO2012/110254
PCT Pub. Date: Aug. 23, 2012

(65) Prior Publication Data
US 2014/0222019 A1 Aug. 7, 2014

(30) Foreign Application Priority Data
Feb. 17, 2011 (DE) .......................... 10 2011 011 497

(51) Int. Cl.
*A61B 17/00* (2006.01)
*A61B 19/00* (2006.01)
(Continued)

(52) U.S. Cl.
CPC .......... *A61B 19/2203* (2013.01); *A61B 34/30* (2016.02); *A61B 34/70* (2016.02);
(Continued)

(58) Field of Classification Search
CPC ... A61B 19/2203; A61B 19/20; A61B 19/201; A61B 19/22; F16H 7/00; F16H 7/02
(Continued)

(56) References Cited

U.S. PATENT DOCUMENTS 5,046,375 A * 9/1991 Salisbury, Jr. ........... B25J 9/046
414/7
5,797,900 A * 8/1998 Madhani ................... B25J 3/04
606/1
(Continued)

FOREIGN PATENT DOCUMENTS

EP 1 886 630 B1 2/2008

OTHER PUBLICATIONS

European Patent Office; Search Report in International Patent Application No. PCT/EP2012/000719 dated Jan. 3, 2013; 12 pages.
(Continued)

*Primary Examiner* — Katherine M Shi
*Assistant Examiner* — Mohamed Gabr
(74) *Attorney, Agent, or Firm* — Wood Herron & Evans LLP

(57) ABSTRACT

A surgical instrument according to the invention, particularly a robot-guided surgical instrument, has a shaft end (1), a tool holder (2), which is mounted on the shaft end so as to be able to rotate about a yaw axis (G), and a tool (3) with a main lever (3A), in particular a blade and/or jaw, which is mounted on the tool holder so as to rotate about a pitch axis (N), and a gear transmission with a drive wheel (31), which is mounted on the tool holder so as to be rotatable about an input gear axis (G) by a driving means (200), and, in force-fit and/or form-fit connection therewith, an output wheel (30), which is mounted on the tool holder so as to rotate about an output gear axis (N) and by means of which the tool is rotatable about the pitch axis, or a wraparound transmission with a drive wheel, which is mounted on the tool holder so as to be rotatable about an input gear axis by a driving means, an output wheel, which is mounted on the tool holder so as to be able to rotate about an output gear axis and by means of which the tool is rotatable about the pitch axis, and
(Continued)

Figure 1:
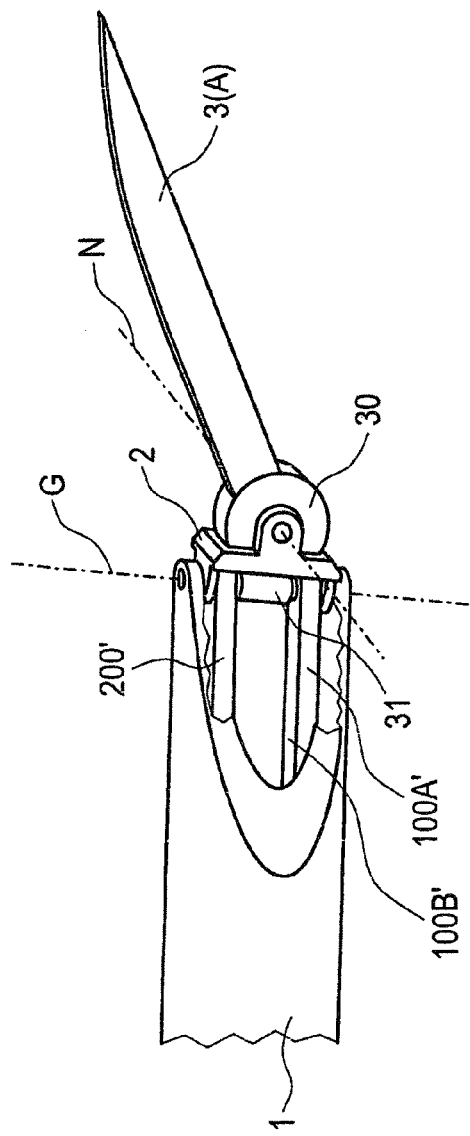

two traction strands which are different from the drive means, are in particular connected and couple drive wheel and output wheel, or a differential transmission with an output wheel (350; 350A), which is mounted on the tool holder so as to be able to rotate about an output gear axis and by means of which the tool is rotatable about the pitch axis, wherein two traction strands are mutually offset in the direction of the output gear axis, in particular on both sides of the yaw axis, run in opposite directions from the output wheel and/or onto the output wheel and/or are both secured on the output wheel and/or are different from a driving means by which a drive wheel (110), firmly or operatively connected to the tool holder, is rotatable about the yaw axis.

24 Claims, 22 Drawing Sheets

(51) Int. Cl.
　　*A61B 34/00*　　　(2016.01)
　　*A61B 17/29*　　　(2006.01)
　　*A61B 34/30*　　　(2016.01)

(52) U.S. Cl.
　　CPC ...... *A61B 34/71* (2016.02); *A61B 2017/2927* (2013.01); *A61B 2034/302* (2016.02)

(58) Field of Classification Search
　　USPC ............... 606/1, 130; 464/69; 227/175.1; 474/148, 61, 62, 139; 74/490.01, 74/490.04–490.06; 901/19–21, 25, 27, 901/28, 29
　　See application file for complete search history.

(56) References Cited

U.S. PATENT DOCUMENTS

| | | | | |
|---|---|---|---|---|
| 5,976,122 | A * | 11/1999 | Madhani | A61B 17/00234 606/1 |
| 6,331,181 | B1 * | 12/2001 | Tierney | G06Q 30/02 600/429 |
| 6,371,952 | B1 | 4/2002 | Madhani et al. | |
| 6,394,998 | B1 * | 5/2002 | Wallace | 606/1 |
| 6,676,684 | B1 * | 1/2004 | Morley | 606/205 |
| 6,840,938 | B1 * | 1/2005 | Morley | A61B 18/1445 606/50 |
| 7,101,363 | B2 * | 9/2006 | Nishizawa | A61B 17/062 606/1 |
| 7,169,141 | B2 * | 1/2007 | Brock | A61B 90/36 606/1 |
| 7,540,867 | B2 * | 6/2009 | Jinno | 414/7 |
| 8,540,748 | B2 * | 9/2013 | Murphy | 606/205 |
| 9,002,518 | B2 * | 4/2015 | Manzo | A61B 1/00149 700/245 |
| 9,161,772 | B2 * | 10/2015 | Hyodo | B25J 13/02 |
| 9,173,643 | B2 * | 11/2015 | Morley | A61B 17/062 |
| 9,204,923 | B2 * | 12/2015 | Manzo | A61B 18/1445 |
| 2003/0100892 | A1 * | 5/2003 | Morley | A61B 17/062 606/1 |
| 2003/0208186 | A1 * | 11/2003 | Moreyra | 606/1 |
| 2007/0023477 | A1 * | 2/2007 | Whitman | A61B 17/07207 227/175.1 |
| 2007/0288044 | A1 * | 12/2007 | Jinno | A61B 17/29 606/174 |
| 2008/0039255 | A1 * | 2/2008 | Jinno | A61B 17/062 474/148 |
| 2008/0039256 | A1 * | 2/2008 | Jinno | 474/148 |
| 2008/0108443 | A1 * | 5/2008 | Jinno | 464/69 |
| 2008/0183193 | A1 * | 7/2008 | Omori | A61B 17/29 606/130 |
| 2008/0245175 | A1 * | 10/2008 | Jinno | B25J 9/1641 74/490.01 |
| 2009/0031842 | A1 * | 2/2009 | Kawai | A61B 17/29 74/490.01 |
| 2009/0110533 | A1 * | 4/2009 | Jinno | 414/783 |
| 2009/0112229 | A1 * | 4/2009 | Omori | A61B 17/29 606/130 |
| 2009/0112230 | A1 * | 4/2009 | Jinno | B25J 9/104 606/130 |
| 2009/0216249 | A1 | 8/2009 | Jinno et al. | |
| 2010/0198253 | A1 * | 8/2010 | Jinno | A61B 17/29 606/205 |
| 2010/0228283 | A1 * | 9/2010 | Jinno | A61B 17/2909 606/205 |
| 2013/0090194 | A1 * | 4/2013 | Ferlay | B25J 9/104 474/64 |
| 2014/0222019 | A1 * | 8/2014 | Brudniok | A61B 19/2203 606/130 |

OTHER PUBLICATIONS

German Patent Office; Search Report in German Patent Application No. 10 2011 011 497.1 dated Jan. 3, 2012; 6 pages.

\* cited by examiner

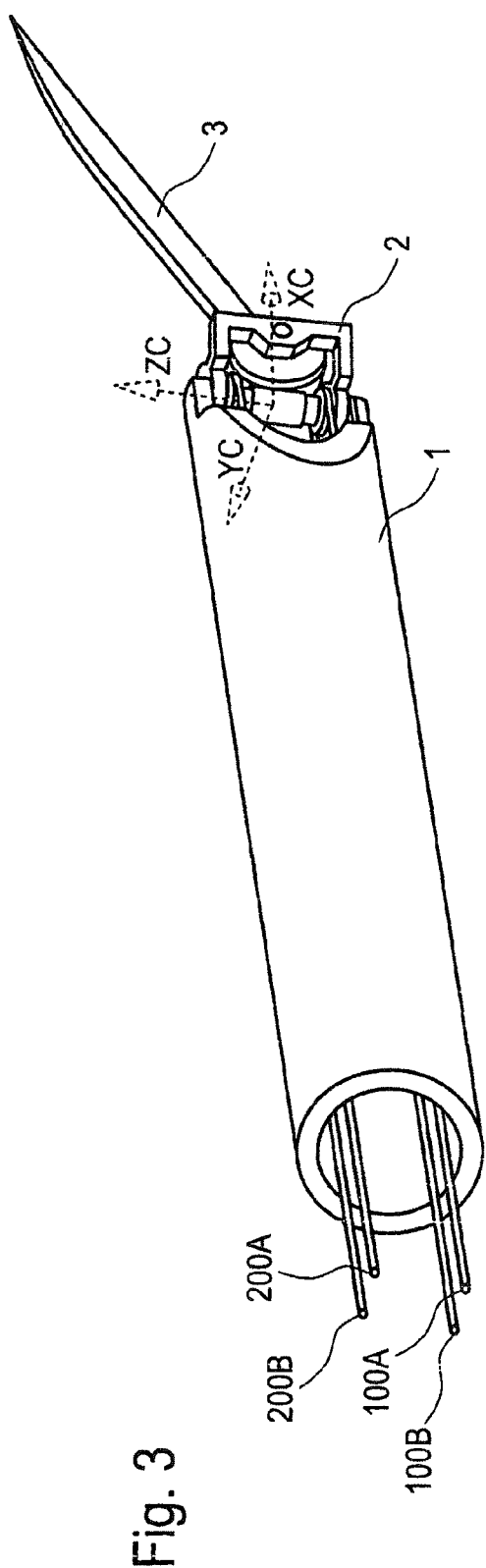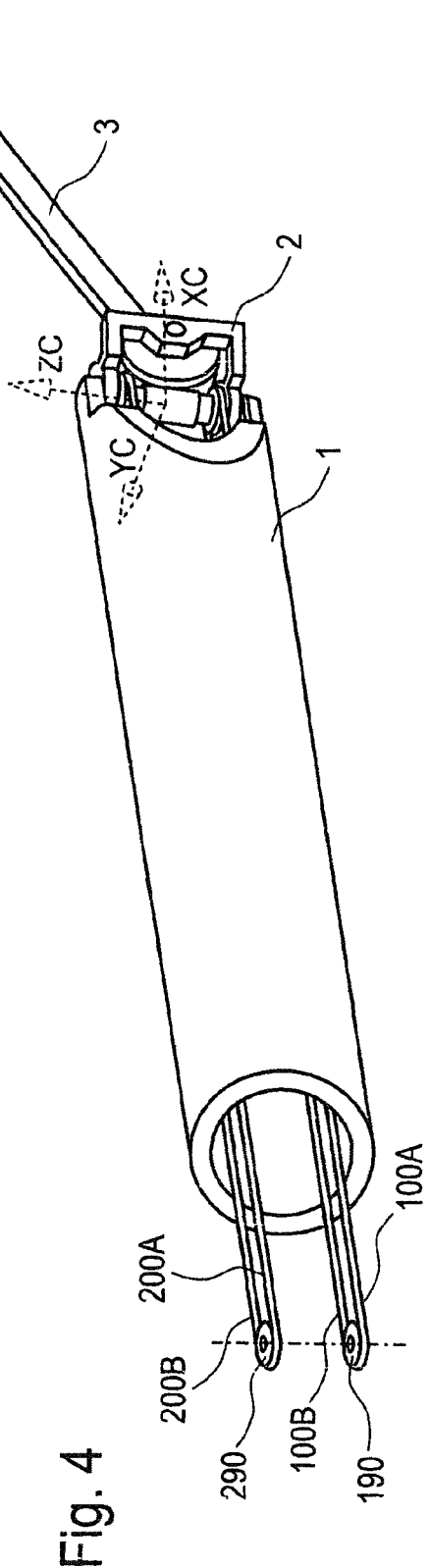

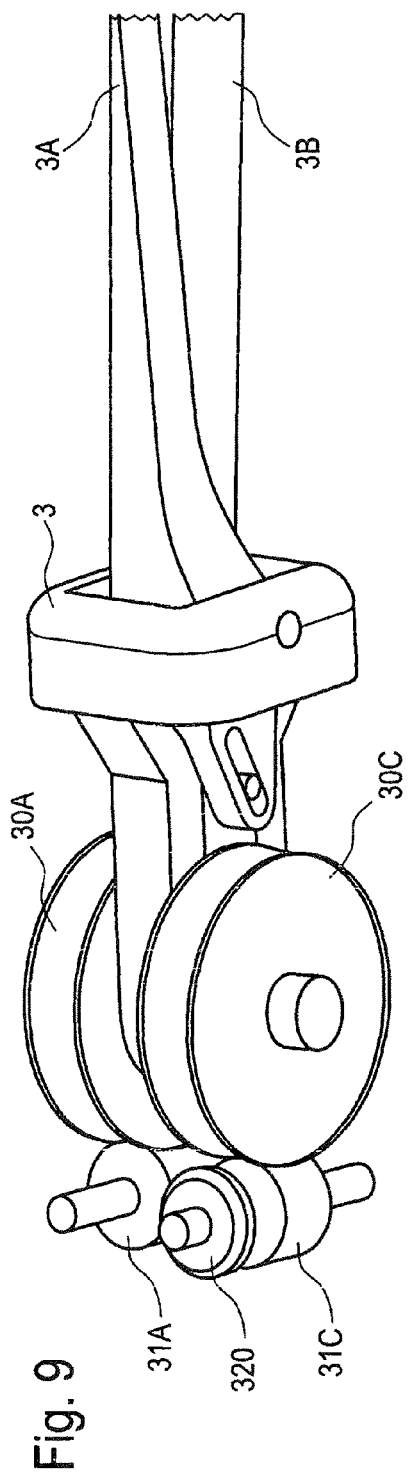
Fig. 9
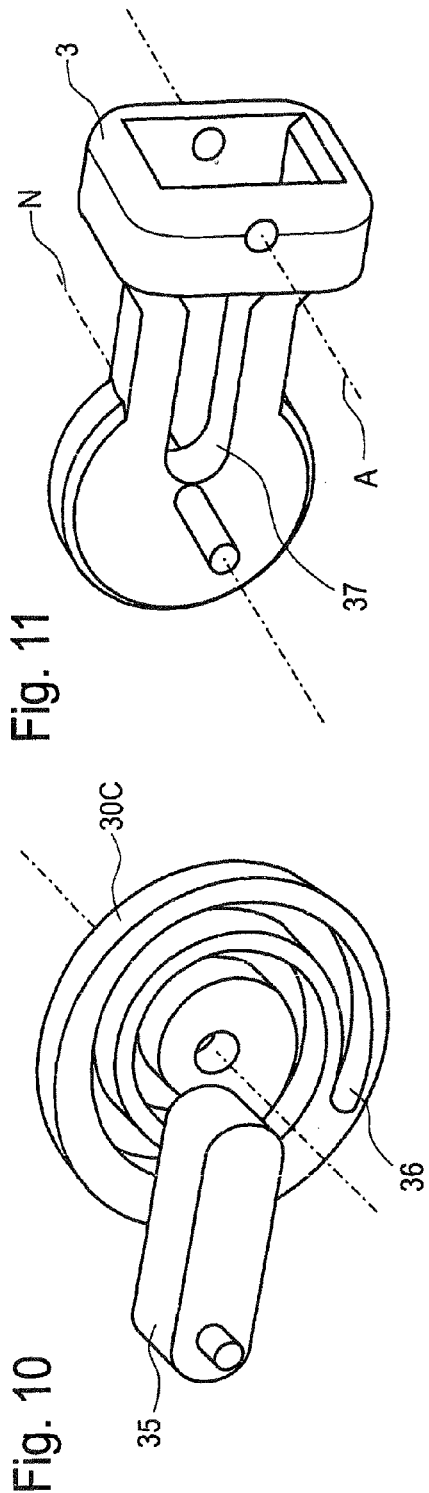
Fig. 11
Fig. 10

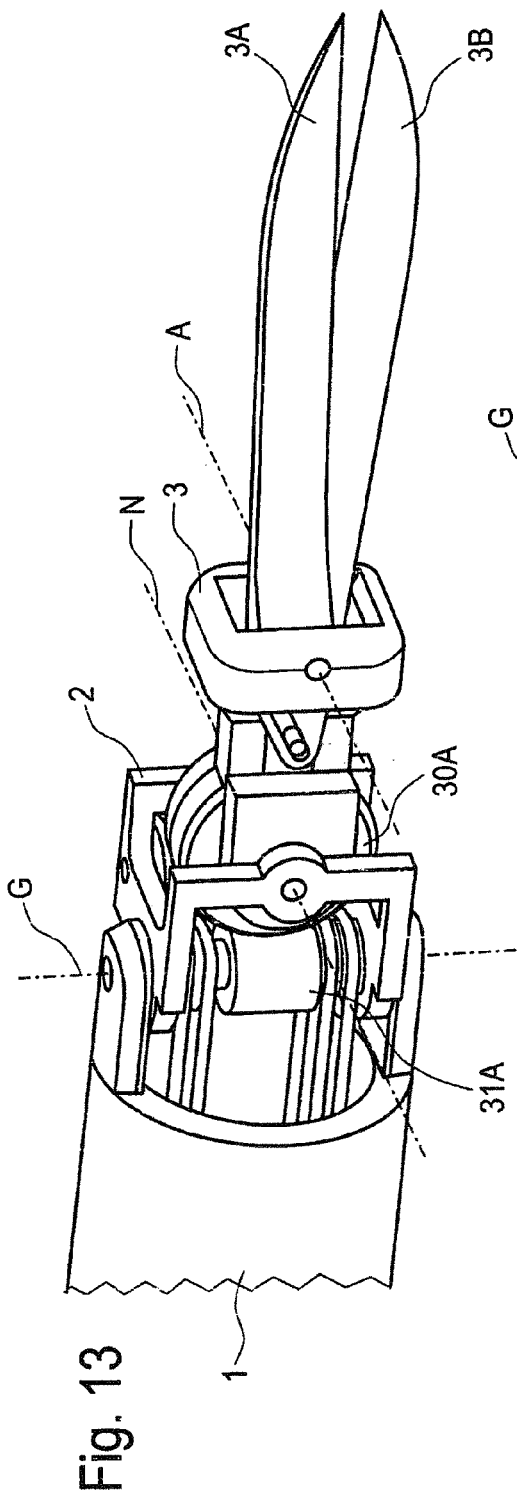
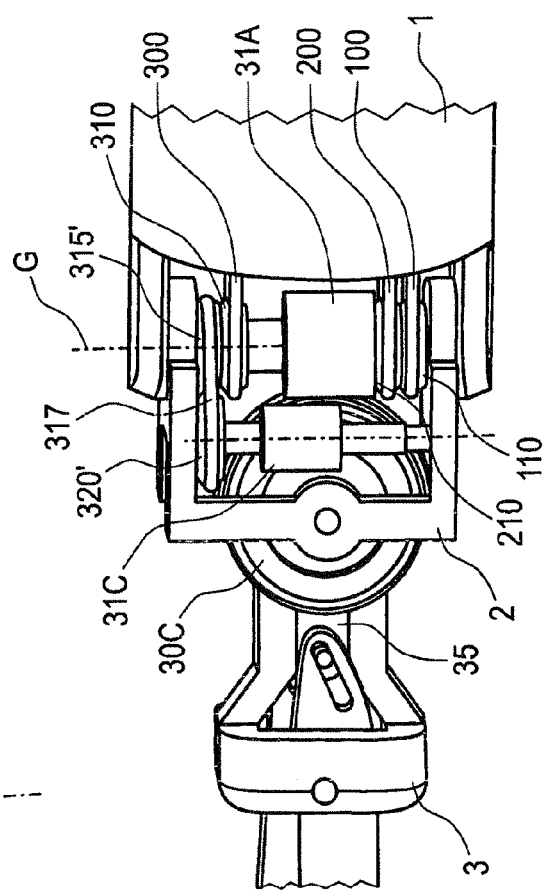
Fig. 13
Fig. 14

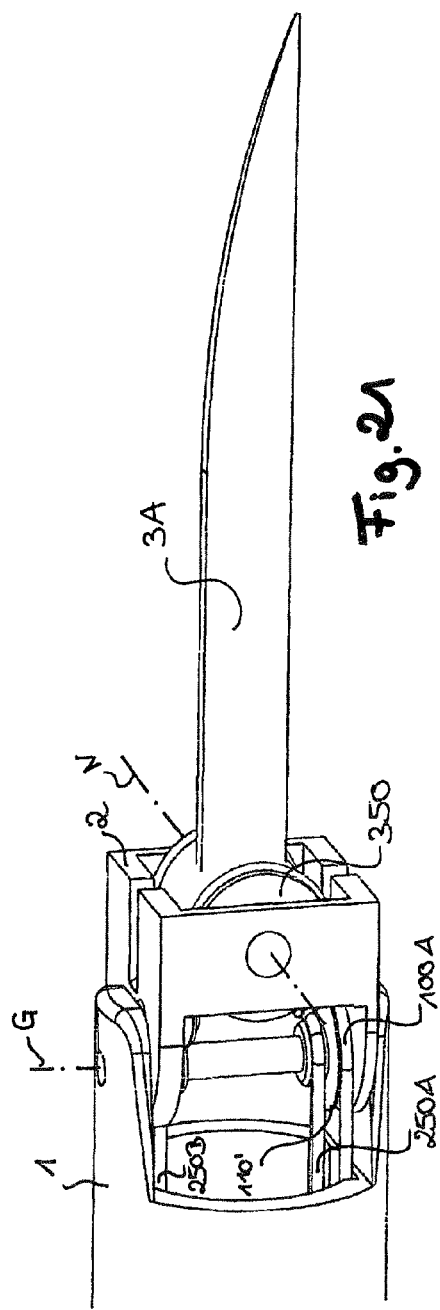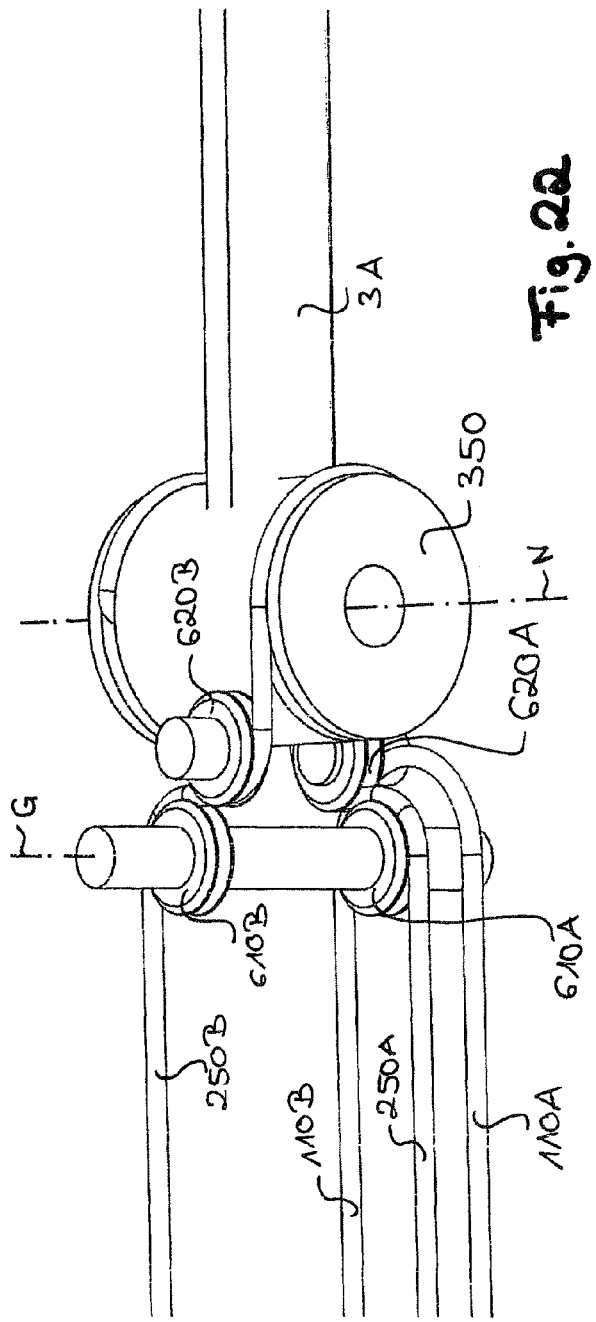

SURGICAL INSTRUMENT

The present invention concerns a surgical instrument, particularly a robot-guided surgical instrument, preferably for minimally invasive surgery, having a shaft end, a tool holder, which is mounted on the shaft end so as to be rotatable about a yaw axis, and a tool having at least one lever, in particular a blade and/or jaw, which is mounted on the tool holder so as to be rotatable about a pitch axis.

For some years now, minimally invasive surgical operations, in particular, in which one or more tools, disposed on distal ends of a surgical instrument are inserted in the patient, preferably by means of trocars, in which the instruments move by means of teleoperated robots controlled by the surgeon.

U.S. Pat. Nos. 6,371,952 and 7,169,141 propose surgical instruments for this purpose in which a tool holder and two levers of a tool mounted therein can rotate about a yaw or pitch axis by means of disks with cords wrapped around them.

The objective of the present invention is to create a surgical instrument having an alternative actuation.

This objective is attained by means of an instrument having the characteristics of Claims 1, 4 or 6, respectively. The dependent Claims relate to advantageous further developments.

A surgical instrument according to the invention exhibits a shaft having a shaft end, and a preferably cage-like, i.e. defined substantially by bar-shaped parts, tool holder, which is mounted on the shaft end so as to be rotatable about a yaw axis. The range of rotation of the tool holder is at least 180° in a preferred design, preferably at least 230°. The shaft end can be connected in a rigid manner to the, preferably robot-guided, shaft, and in particular, it can be designed to be an integral part thereof. Likewise, in order to represent a turning degree of freedom about a longitudinal axis of the shaft, it can be connected in an articulated manner to the shaft, and can be moveable by means of a drive means.

A tool, having at least one, preferably two or more, levers, is mounted on the tool holder so as to be rotatable about a pitch axis. The range of rotation for the tool is at least 180°, preferably 200°, in a preferred design. The yaw and pitch axes cross one another, preferably—at least substantially—at a right angle. The yaw and pitch axes can exhibit an intersection point thereby, i.e. where they cross each other, or they can be skewed, i.e. without an intersection, such that they pass one another at a spacing of the axes, such that presently, in general, two non-parallel axes are indicated, in particular, as crossing axes. Preferably, a drive wheel is rigidly or functionally connected to the tool holder, which can be rotated about the yaw axis by means of a drive means. By turning this drive wheel, which in the following is also referred to as the tool holder wheel, by means of the drive means, the tool holder can be rotated about the yaw axis.

One or more levers can be rigidly connected to the tool, in particular, they can be designed as an integral part thereof, and can, for example, exhibit a blade of a scalpel or a jaw of a forceps. In addition, or alternatively, one or more levers may be moveable in relation to the tool, in particular, such that they can rotate, and can, for example, exhibit the blades of a scissors, or the jaws of a forceps. The range of rotation of one or more levers is at least 180°, preferably 200°, in a preferred design.

In particular, two levers, which are rotatably mounted on the tool, or a lever, rotatably mounted on the tool and a lever rigidly connected thereto or the tool holder, can act together in the manner of a scissors or a forceps. Additionally, or alternatively, one or more levers can be mounted in a translational manner, in order to represent, for example, a moveable stylus. The term "lever" thus indicates in the present case, independently of its geometry, in particular, a part of the tool having a functional surface.

According to a first aspect of the present invention, the surgical instrument exhibits a transmission with a drive wheel, which is mounted on the tool holder such that it can rotate about an input transmission axis by means of a drive means, and having an output wheel that is in a force-fitting and/or form-locking connection therewith, mounted on the tool holder so as to be rotatable about an output transmission axis, and by means of which, the tool can be rotated about the pitch axis. For purposes of a concise and consistent representation, this gear transmission shall also be referred to as a tool-transmission in the following.

In particular, in order to implement a further degree of freedom, in a preferred development the instrument exhibits at least one further transmission having a further drive wheel, which is mounted on the tool holder so as to be rotatable, by means of a further drive means, about another input transmission axis, and an output wheel connected in a force-fitting and/or form-locking manner thereto, which is mounted on the tool holder so as to be rotatable about another output transmission axis, and by means of which, a further lever of the tool can be rotated about a further tool axis.

The tool transmission and/or the further transmission can each be designed, in particular, as worm, screw, bevel, hypoid, crown, or friction gear transmissions, such that its input and output transmission axes cross one another, in particular—at least substantially—at a right angle, with or without an intersection. With a worm, screw, bevel, hypoid or crown gear transmission, the input and output drive are connected to one another in a form-locking manner by means of combing teeth, and with a friction gear transmission, they are connected in a frictional or force-locking manner. For a concise and consistent representation, a worm gear, a bevel gear and suchlike, having a rotational body with a front and/or circumferential gearing, or friction surface, respectively, are referred to in general as an input or output drive wheel as set forth in the present invention. An axis is understood in the present invention, in particular, as a kinematic axis of rotation, wherein this can be structurally defined, in particular, by a floating shaft, or a shaft supported at both ends, or by a hub, which rotates about a structural cylinder, also referred to as an axle.

According to a second aspect of the present invention, the surgical instrument exhibits a wraparound transmission having an input drive wheel, mounted on the tool holder so as to be rotatable about an input transmission axis, an output drive wheel, mounted on the tool holder so as to be rotatable about an output transmission axis, by means of which, the tool can rotate about the pitch axis, and having two, in particular, interconnected traction strands, which differ from the drive means, which couple the input and output wheels. For a concise and consistent representation, this wraparound transmission shall also be referred to in the following as the tool wraparound transmission.

In particular, in order to obtain a further degree of freedom, in a preferred development the instrument exhibits at least one further wraparound transmission, with a further drive wheel, which is mounted on the tool holder such that it can rotate about a further input transmission axis by means of a drive means, and a further output drive wheel, which is mounted on the tool holder such that it can rotate about a further output transmission axis, and by means of which, a further lever, in particular, a blade and/or jaw of the tool can rotate about a further tool axis, and having two further, in particular, interconnected traction strands, differing from the drive means, which couple the further input and output drive wheels.

The input and output drive wheels of the tool-wraparound transmission and/or the further wraparound transmission, in another preferred development, are each encircled, on at least a portion of their respective circumferences, by a closed traction means, connected to the two drive wheels, in particular, by means of traction strands, designed to be integral to one another, in a frictional manner, in particular by means of a traction cord, a friction belt or suchlike, or in a form-locking manner, in particular by means of a toothed belt or suchlike. Two interconnected traction strands can be formed, in particular, by means of a continuous traction means, such as a cord, cable, or belt, for example, the two ends of which are permanently, or releasably connected to one another, such that the traction means, or the two interconnected traction strands, form one or more closed loops. For a consistent representation, a roller or disk, a rotating body in general, having a contact surface for a frictional or form-fitting force transfer to the traction strands, is also referred to as an input or output drive wheel, as set forth in the present invention.

According to a third aspect of the present invention, the surgical instrument exhibits a differential transmission, having an output drive wheel, which is mounted on the tool holder so as to be rotatable about an output transmission axis, and by means of which the tool can rotate about the pitch axis. For a concise and consistent representation, this differential transmission shall also be referred to in the following as the tool-differential transmission. Two traction strands run, offset to one another, in the direction of the output transmission axis, in particular on both sides of the yaw axis, in opposing directions from the output drive wheel, or toward said drive wheel, respectively. In a preferred development, both traction strands can be attached in a fixed manner to the output drive wheel. Additionally, or alternatively, a further drive means can be provided for rotating a tool holder wheel, rigidly or functionally connected to the tool holder, in addition to the traction strands of this differential transmission, and differing therefrom.

Two traction strands run, in particular as set forth in the present invention, in opposing directions from an output drive wheel, or toward said drive wheel, respectively, when a rotation of the output drive wheel about its output transmission axis corresponds to a divergence of the one traction strand from the output drive wheel, and a convergence of the other traction strand toward the output drive wheel, or, when a rotation of the output drive wheel can be obtained by a tractive force toward one traction strand, and an opposite rotation of the output drive wheel by a tractive force toward the other traction strand, respectively. In the present case, in particular, a convergence or divergence in two spatial halves moving together with the tool holder is referred to as being on both sides of the yaw axis, which are separated from one another by means of a plane moving together with the tool holder, in which the yaw axis lies. A traction strand is rigidly attached to an output drive wheel, in particular as set forth by the third aspect, when a section of the traction strand is—at least substantially—immobile in relation to the output drive wheel, in particular—at least substantially—when no slippage can occur. In particular, a free end of the traction strand can be connected rigidly, in particular, form-fitting, frictionally and/or firmly bonded, to the output drive wheel. In one design, a free end of the traction strand is inserted for this purpose in a hole on, in particular, in, the output drive wheel, which runs preferably, at least substantially, radially or tangentially, and is caulked, clamped, glued or welded, for example, in place there. Likewise, two traction strands of a differential transmission can also be connected to one another, in particular, they can be designed as integral to one another, and inserted collectively, as a lug, for example, in a hole of this type in the output drive wheel, and caulked, clamped, glued or welded, for example, therein.

In particular, in order to actuate a further degree of freedom, in a preferred development, the instrument exhibits at least one further differential transmission having a further drive wheel, which is rotatably mounted on a further output transmission axis on the tool holder, and by means of which another lever, in particular a blade and/or jaw, of the tool can rotate about a further tool axis, wherein two further traction strands are offset in relation to one another in the direction of the further output transmission axis, in particular, on both sides of the yaw axis, running in opposite directions from the further output drive wheel, or toward it, respectively, and which can be rigidly attached to the further output drive wheel in a preferred further development. Additionally or alternatively, these traction strands of this further differential transmission may differ from a drive means, which is additionally provided for rotating a tool holder wheel that is rigidly or functionally connected to the tool holder.

In one embodiment, a traction strand of the tool-differential transmission and a traction strand of a further differential transmission can run on one side of the yaw axis and the other traction strand of the tool-differential transmission and the other traction strand of the further differential transmission can run on the other side of the yaw axis from or toward the respective output drive wheel, such that the two traction strands of this differential transmission in each case run toward or away from the differential transmission, respectively, on both sides of the yaw axis. In another embodiment, both traction strands of the tool-differential transmission can run on one side of the yaw axis of the output drive wheel, toward or away from said output drive wheel, and both traction strands of a further differential transmission can run on the other side of the yaw axis, away from or toward the further output drive wheel, respectively, such that the two traction strands of this differential transmission are each on one side of the yaw axis, and the traction strand pair of the tool-differential transmission and the further differential transmission run on both sides of the yaw axis toward or away from the respective output drive wheel, respectively.

After running toward or away therefrom, the two traction strands of a differential transmission, in particular the two traction strands of the tool-differential transmission, and/or the two traction strands of a further differential transmission can be guided, in particular, by mean of one or more guide wheels, on the same side of the yaw axis, or on both sides of the yaw axis, past said transmissions. For this, traction strands, as shall be explained below, can run, in particular, can be guided, between the output transmission and yaw axes, from the one to the other side of the yaw axis.

In particular, in order to by pass the yaw axis with traction strands according to the second or third aspect, in a preferred design one or more, in particular, all traction strands of the differential transmission(s) are guided by means of one, two or more guide wheels for each, which are preferably mounted on the tool holder with one rotational degree of freedom each about a guidance rotational axis.

Preferably, a guidance rotational axis, about which a guide wheel is rotatably mounted on the tool holder, is flush with the yaw axis. For a concise, consistent depiction, this guidance rotational axis shall also be referred to in the following as an input transmission axis of the differential transmission. In a preferred further development, a further guidance rotational axis of a further guide wheel, which is at least partially encircled by the traction strand, preferably in the opposite direction of the input transmission axis-guide wheel, is displaced parallel to the yaw axis, and/or tilted.

Preferably, a further guide wheel of this type, which guides the one traction strand of a differential transmission, and a further guide wheel of this type, which guides the other traction strand of this differential transmission, are disposed on both sides of the yaw axis, in order to offset the two traction strands in opposite directions perpendicular to the yaw axis. Additionally, or alternatively, at least one further guidance rotational axis of a further guide wheel, which guides the one further traction strand of a differential transmission, is tilted against the yaw axis, tilted in the opposite direction in relation to a further guidance rotational axis of a further guide wheel, which guides the other traction strand of this differential transmission, to offset the respective traction strand, with a component in the direction of the yaw axis. An opposite tilting is understood to mean, in the present case, in particular, that the two further guide rotational axes encompass the yaw axis with angles having opposite signs, preferably to the same degree.

In a preferred design, a traction strand, in particular of a wraparound transmission according to the second aspect, or of a differential transmission according to the third aspect, preferably between the yaw and the pitch axes, forms an angle with the yaw and/or pitch axis, which is greater than 0°, and in particular, is greater than 15°, and less than 90°, in particular, less than 75°. The other traction strand of this transmission preferably forms—at least substantially—a right angle with the yaw and/or pitch axis. In particular, a traction means having a circular cross-section is suitable for this, because it can make contact at different regions of the circumference of the input and output drive wheel, without becoming twisted.

In particular, in order to guide the traction strand described above, which runs at an angle to the yaw and/or pitch axis, between the input and output wheels, a traction strand is guided by means of one, two or more guide wheels in a preferred design. Preferably, a guidance rotational axis, about which a guide wheel is rotatably mounted on the tool holder, is tilted at an angle to the pitch and/or yaw axis, which is greater than 0°, preferably greater than 15°, and less than 90°, preferably less than 75°.

In a preferred design, another guide wheel is disposed adjacent to a guide wheel or an output drive wheel in such a manner that the two wheels form a channel between them which—at least substantially—corresponds to a cross-section dimension, in particular, a diameter, of a traction strand. In this manner, a traction strand running toward, or away from the guide or output drive wheel, can be cleanly guided, in particular when the tool holder moves about the yaw axis.

An advantageous transmission behavior can be obtained according to the first, the second, and the third aspects of the present invention. In particular, the dynamics of a gear, wraparound or differential transmission can be better modeled in a preferred further development than with the instruments known so far, and thus facilitate the necessary indirect, model-based force measurement for a force feedback to the operator due to the drive forces. Accordingly, in a preferred further development, it is provided that model-based forces, transmitted from measured drive forces and/or torques, in particular, forces or torques transmitted from drives or drive means, can be determined for forces or torques occurring on one or more levers of the tool. Additionally, or alternatively, an instrument according to the first, second, or third aspect of the present invention can enable a greater rotational range in one or more degrees of freedom and/or a more precise actuation.

The advantageous designs described in the following can further develop the first, second, and/or third aspect.

According to one advantageous design, the input transmission axis of the tool-gear, -wraparound, or -differential transmissions, respectively, and/or the further gear, wraparound, or differential transmission, respectively—at least substantially—can be parallel to the yaw axis of the tool holder, in particular, it can be flush with said axis, or can have a spacing between the axes. Additionally, or alternatively, the output transmission axis of the tool-wheel, -wraparound, or -differential transmission, respectively, and/or the further gear, wraparound, or differential transmission—at least substantially—can be parallel to the pitch axis, in particular, it can be flush with said axis.

In a preferred design, the tool exhibits a tool base body, which is mounted on the tool holder so as to be rotatable about the pitch axis, and is rigidly or functionally connected to the output drive wheel of the tool-gear, -wraparound, or -differential transmission, respectively, and in particular, is designed as an integral part thereof. A functional connection is understood to mean, as set forth in the present invention, in general, particularly a foam- or force-locking, in particular, a frictionally engaged coupling, such that a motion of one body causes a forced motion of the body that is functionally connected thereto. In particular, a functional connection can exhibit a single or multiple step intermediate gear, friction wheel and/or wraparound transmission.

A lever of the tool, also referred to in the following as a base lever, can be rigidly connected to this tool base body, in particular, it can be designed as an integral part thereof, such that this lever is rotated with the tool base body by means of the output drive wheel of the tool-gear, -wraparound, or -differential transmission, respectively, about the pitch axis.

In order to actuate two levers that can move counter to one another, the further lever, which is moved by means of the further gear, wraparound, or differential transmission, respectively, can be mounted on the tool base body in a rotatable manner, and functionally or rigidly connected to the output drive wheel of the further gear, wraparound or differential transmission, respectively, in particular, such that it is designed as an integral part thereof, wherein, in a preferred further development, the further tool axis is—at least substantially—parallel to the pitch axis, and in particular, is flush thereto. In this manner, a scissors or forceps, respectively, can be represented, in particular, the scissors blades, or forceps jaws, respectively, thereof, are formed by the base lever and the tool base body, on one hand, and the, preferably, at least substantially, mirror symmetrical thereto, further lever, on the other hand.

In a preferred design, the tool base body is designed in the form of a spool, wherein traction strands can run toward or away from two spool flanges in opposite directions in a preferred further development of the third aspect. The further lever can, in particular by means of the further output drive wheel of the third aspect, be rotatably mounted on the spool shaft of the tool base body. In a preferred design, the two spool flange halves encase a tool leaf, on which the traction strands run toward or away from, in opposite directions, the spool flange of the other tool leaf, on which the associated traction strands run toward or away, in opposite directions. In another design, the tool base body exhibits an output drive wheel, and a shaft on which the other output drive wheel is rotatably mounted, wherein the two output drive wheels of the spool flanges form a spool, from which, in a preferred further development of the third aspect, the two traction strands of the tool-differential transmission, or the two traction strands of the further differential transmission, respectively, can run toward or away, in opposite directions.

Likewise, in a preferred design, the base lever can be rotatably mounted on the tool base body about a tool axis, which will also be referred to in the following as the base tool axis. In a preferred further development, the further lever of the tool, which can be rotated by means of the further output drive wheel, is also mounted on the tool base body so as to be rotatable about the further tool axis, wherein, in a preferred further development, the base axis, as well as the further tool axis—at least substantially—are parallel, and in particular, flush.

In a preferred further development a rotation spreads the further output drive wheel main and further levers apart from one another. For this, in a preferred further development, a conversion transmission for converting rotational and a translational motions into one another is disposed between the further output drive wheel and the levers of the tool. The conversion transmission exhibits a spiral-shaped link, functionally or rigidly connected to the further output drive wheel in a preferred design, on which a translationally guided sliding body is guided in a form-locking manner. A spiral-shaped link is understood, in particular, to mean a link, which exhibits a groove, which guides a projection of the sliding body, or exhibits a projection, which guides a groove on the sliding body, having a radial spacing varying with the angle of rotation, preferably in a linear manner, such that a rotation of the link displaces the sliding body in a translational manner. The main and further levers preferably exhibit a link guide running in the opposite direction, in which the sliding body is guided in a form-locking manner, and with which a translational motion of the sliding body causes a spreading of the main and further levers apart from one another. In this design, the closing or opening of the tool is advantageously caused by a single drive means. If couplings occur with these drive motions, these can be reversed preferably with the aid of further drive motions.

A drive means can, in general, exhibit two traction strands which run in opposing directions. Two traction strands of a drive means, or a wraparound or differential transmission, which can run in opposing directions, in particular cord, cable, friction, in particular V-belts or toothed belts, can be connected collectively at the input or output drive side, in particular on both sides, to a traction means closed on one or both ends, in particular in such a manner that they are designed to be an integral part thereof. The traction strands can encircle a driven wheel, in particular a tool holder wheel or an input or output drive wheel of a wraparound or differential transmission, in a frictional-locked manner, in part or in multiple windings, such that a tractive motion of a traction strand causes a movement of the other traction strand in the opposite direction, and a rotation of the driven wheel. The traction strands can also be connected to a driven wheel, in particular a tool holder wheel or an input or output wheel of a wraparound or differential transmission in a form- and/or material-locking manner, in that in each case, basically one end of a traction strand is attached to the driven wheel, and the two traction strands are offset to one another on opposite sides of the wheel, in particular in the direction of the rotational axis of the wheel, running toward or away therefrom, respectively, such that in turn, a tractive motion of the one traction strand causes a motion in the opposite direction of the other traction strand, and a rotation of the driven wheel. Preferably, in a zero or neutral position, a wrapping of the driven wheel between the attachment and the run-off of a traction strand amounts to more than 90°, such that the wheel can be rotated more than 90° from the zero position by means of a traction strand, before it is fully run out. Likewise, traction strands connected to one another can be connected to a driven wheel in a form- and/or material-locking manner, in that, for example, a lug is formed in the traction means, and is disposed in an accommodation of a driven wheel.

Additionally, or alternatively, two traction strands can be connected to one another at the input drive end, and encircle, in part or with multiple windings, an output drive wheel of a drive, preferably an electric motor, for example, in a form- or friction-locking manner. Likewise, the two traction strands can also be drawn in separately at the input end, preferably in a synchronized manner in opposing directions. By way of example, two traction strand ends can be attached to two opposing levers in an articulated manner, which are rotated by means of a drive shaft of an electric motor, such that a lever pulls the traction strand connected in an articulated manner thereto, while the other lever releases the other traction strand in the opposite direction, in a synchronous manner. In this manner, a similar actuation can be obtained as that with an output drive wheel, which is encircled by two traction strands connected to one another at the drive end, and which thus likewise actuates said strands in opposing directions. In one design, the two traction strands are connected to segments which are moved along the traction strand axis, in particular, in a linear manner, and are coupled in their movement, in opposing directions. Two traction strands which each exhibit two ends, wherein only one end of a traction strand is connected to one end of the other traction strands, in particular, in an integral manner, are regarded as closed at one end, in particular, and two traction strands that are closed at both ends relates to two traction strands, in particular, wherein both ends of one traction strand are connected to both ends of the other traction strand, in particular in an integral manner.

If further traction strand pairs are present, connected, in particular, to one another at least on the input drive end, in particular in order to actuate a tool holder wheel and/or a further gear, wraparound, or differential transmission, respectively, in addition to traction strands of a tool-gear, -wraparound, or -differential transmission, then, in a preferred design, the rotational axes of actuators can be parallel to one another, or, in particular, be tilted toward one another, in particular at the same angle.

A driven wheel can also be actuated by means of a pushing means connected in an articulated manner thereto, in particular a push rod, which is connected in an articulated manner to a sliding body in the driven wheel, which is guided in a translational manner such that it can be displaced.

The wheel, which is driven by means of a drive means, can, in particular, be an input or output drive wheel of gear, wraparound or differential transmission, or a tool holder wheel. Likewise, it can also be functionally connected to such an intermediate wheel, in particular by means of another traction means or a gearing.

An instrument according to the invention is, in particular, suited for minimally invasive surgery, in which the shaft end is inserted, in part, preferably by means of a trocar, into the body of a patient, and the tool is suitable for actuation in the interior of the patient from outside. In a preferred further development, the instrument is guided by means of a robot, i.e. it is actuated by a robot, and/or as a whole, is moved, in particular with two rotational and one translational degree of freedom about a trocar point. The invention is not, however, limited to this, but rather, an instrument according to the invention can also be used for non-minimally invasive, open surgical operations, and/or be manually guided and actuated by a surgeon. In the preferred application, according to a further aspect of the present invention, a system is proposed, comprising a robot, a surgical instrument according to the invention connected thereto in a permanent or releasable manner, and drives for actuating the drive means of the instrument.

Figure 2:
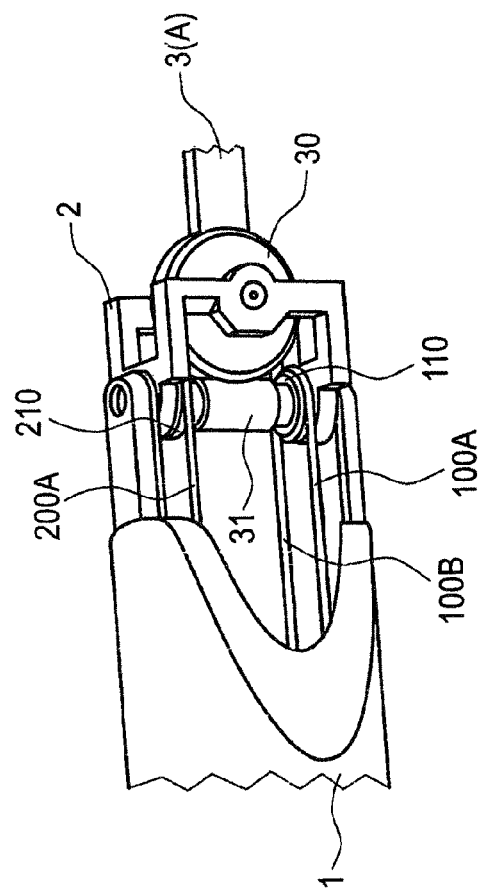
Figure 5:
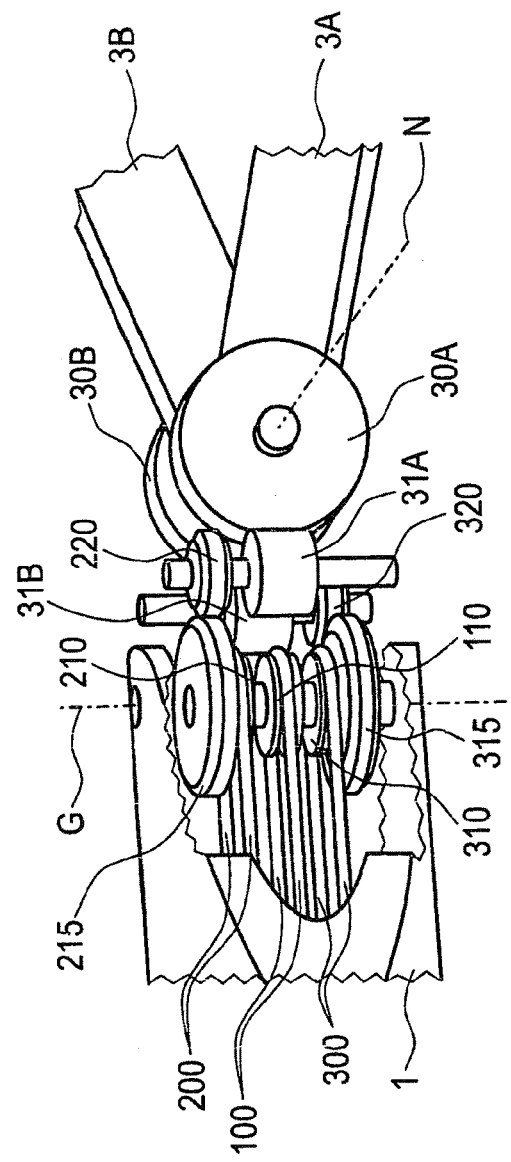
Figure 6:
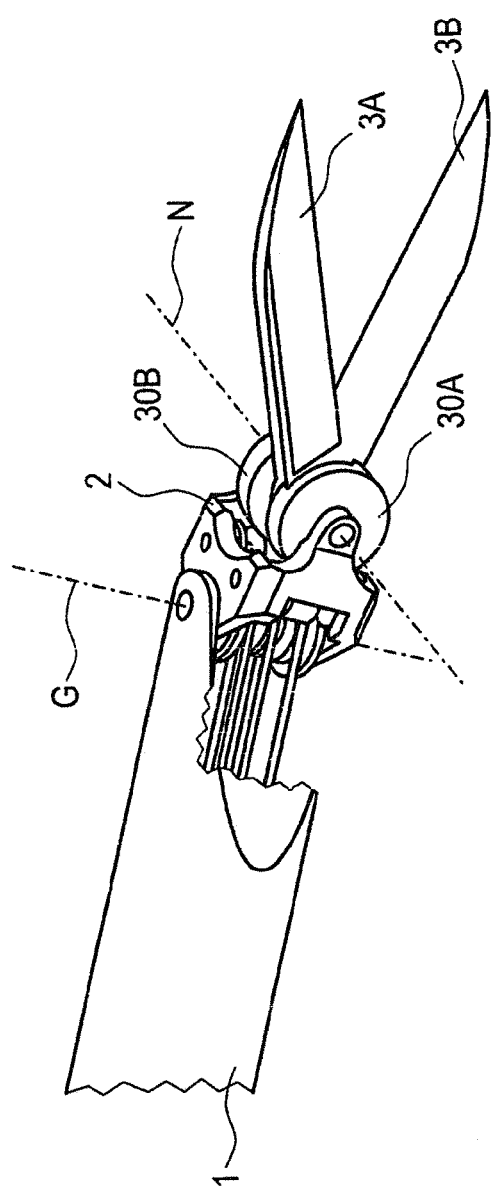
Figures 7, 8:
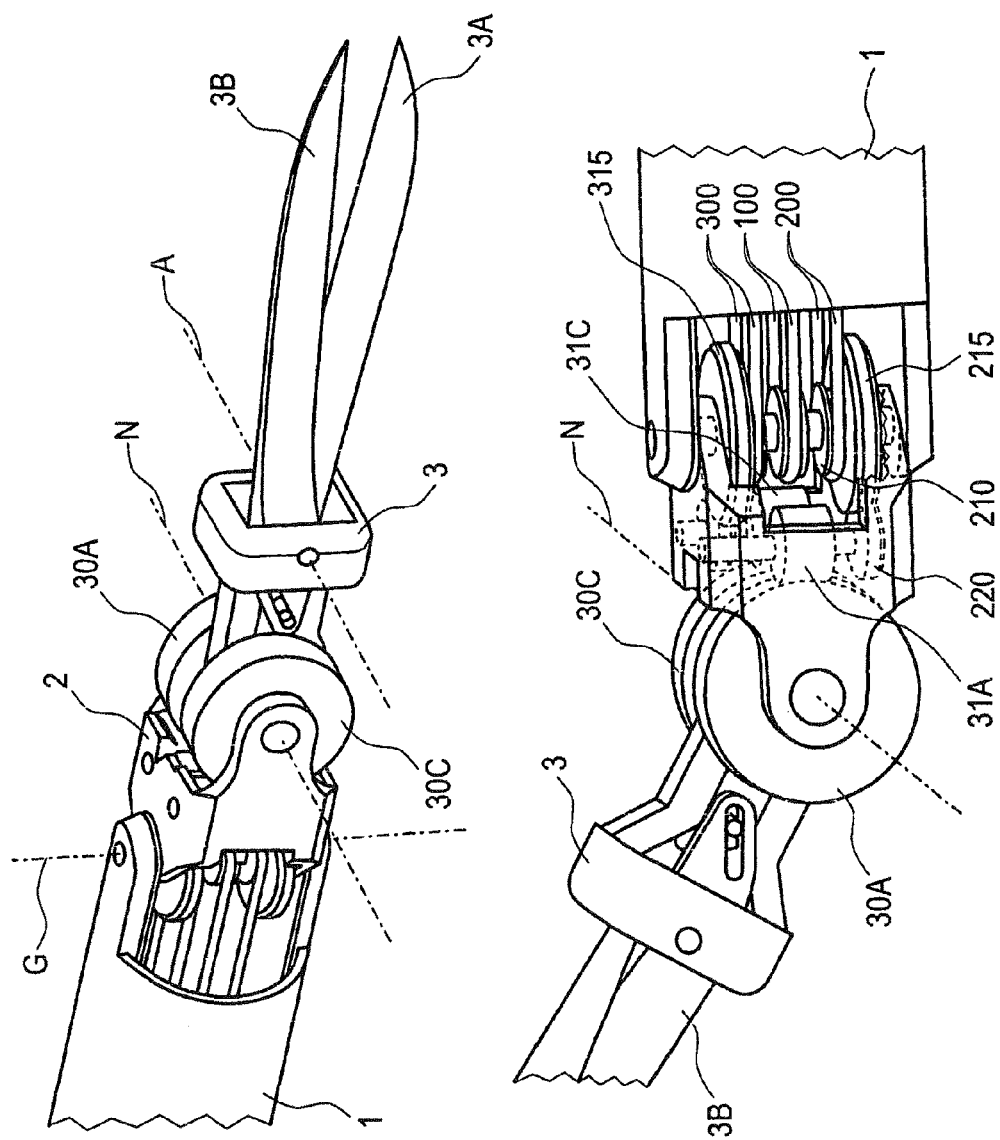
Figure 12A:
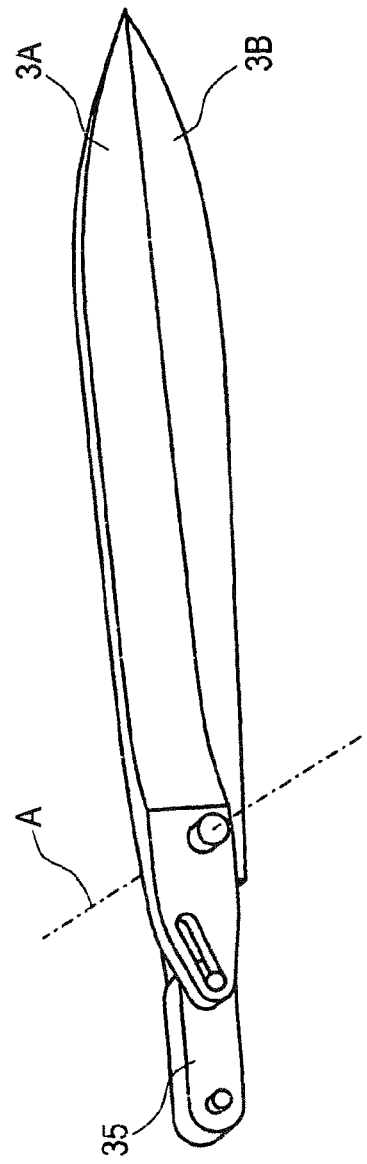
Figure 15:
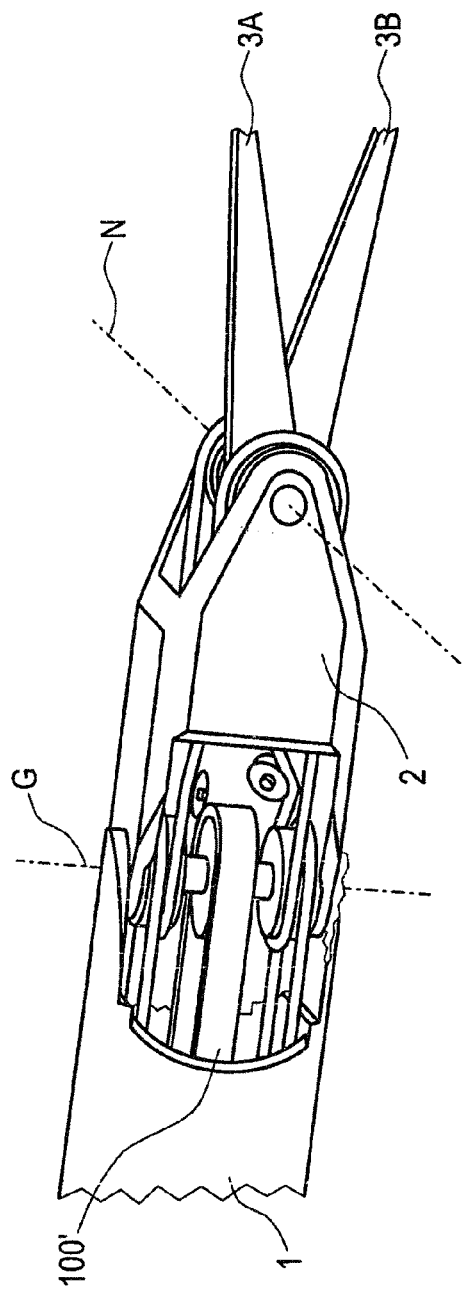
Figure 16:
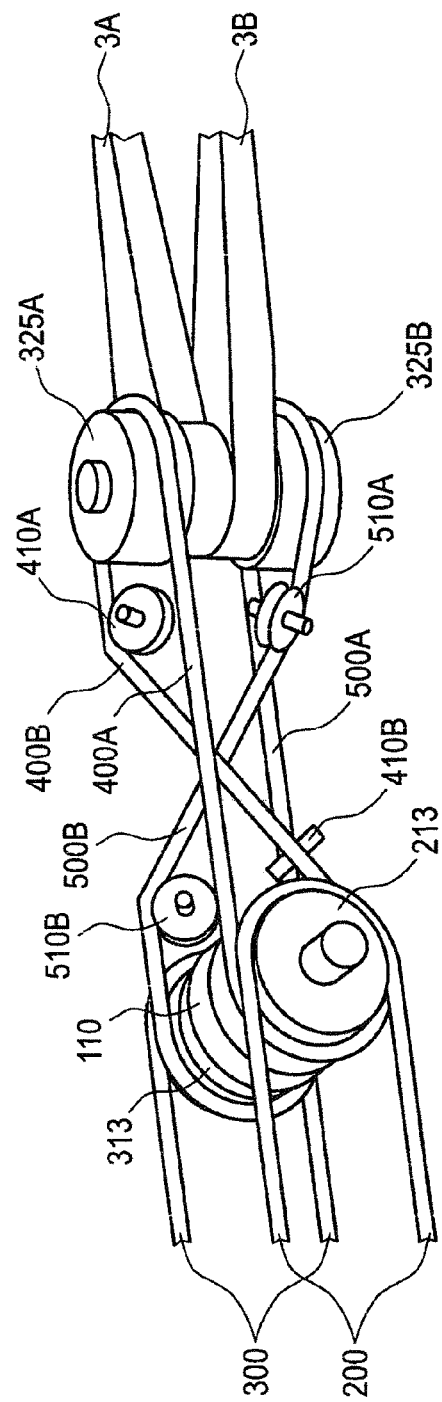
Figure 17:
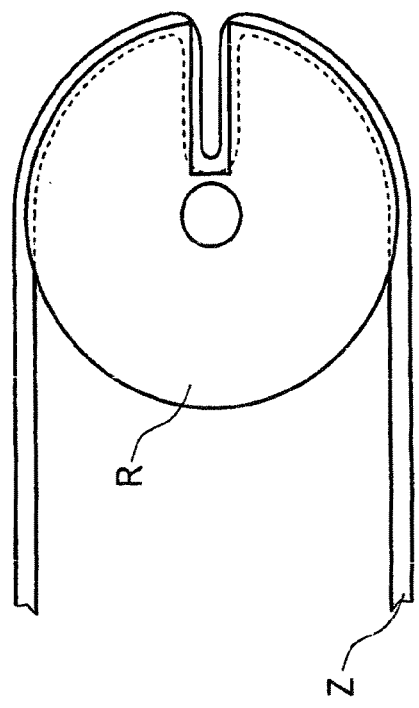
Figure 18:
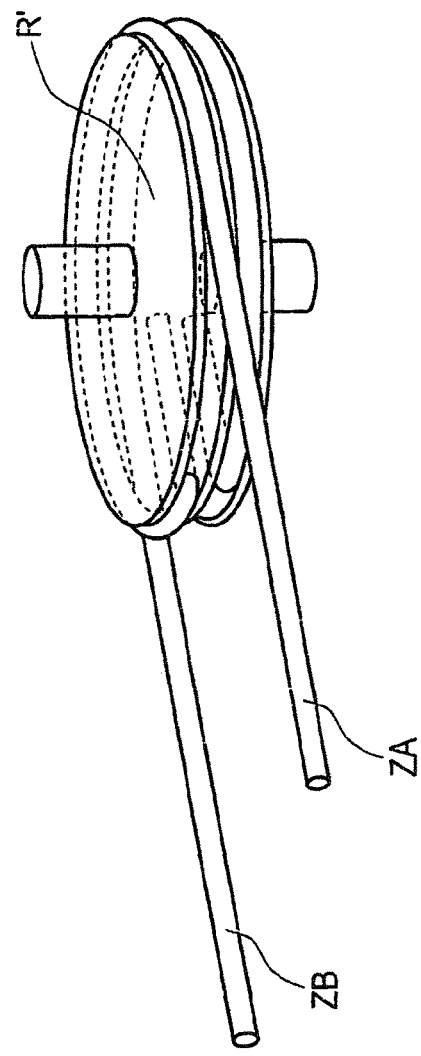
Figure 19:
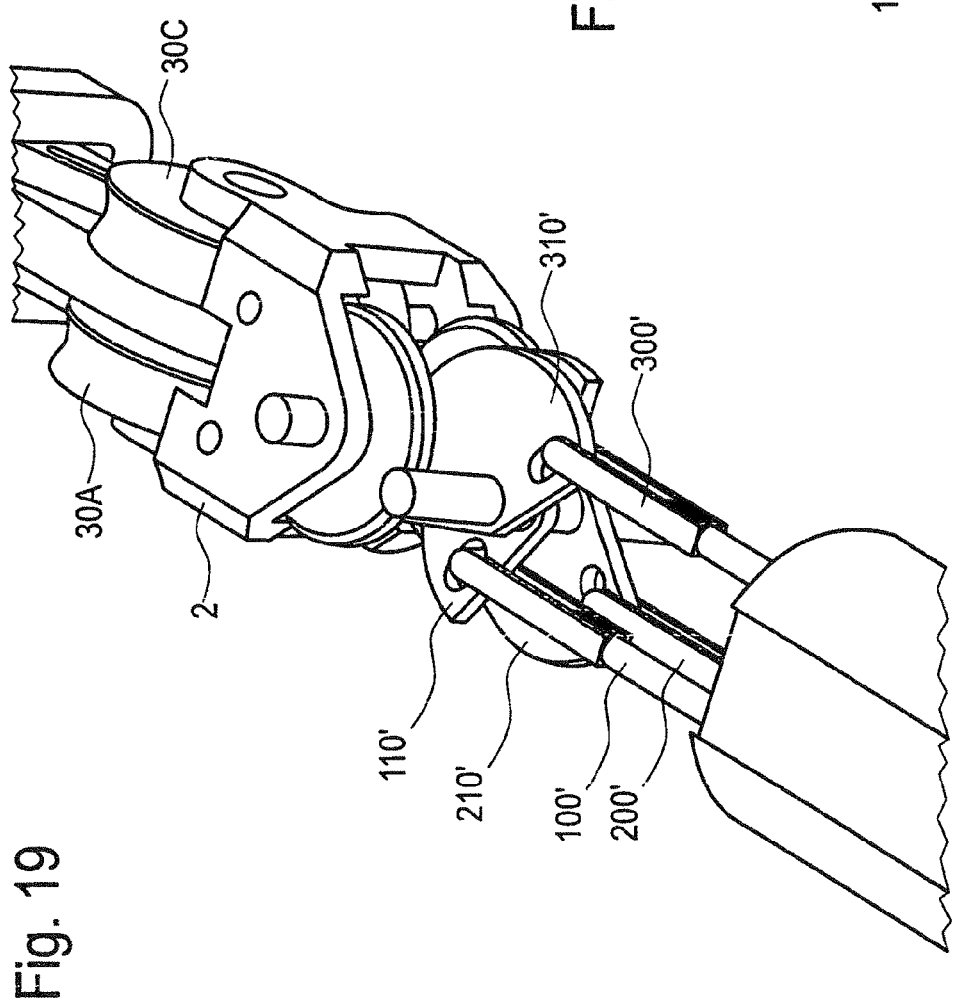
Figure 20:
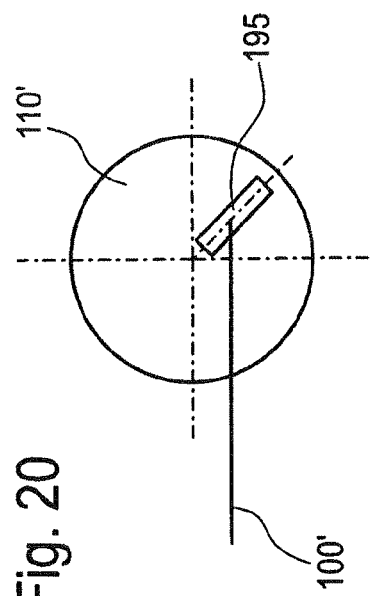
Figure 23:
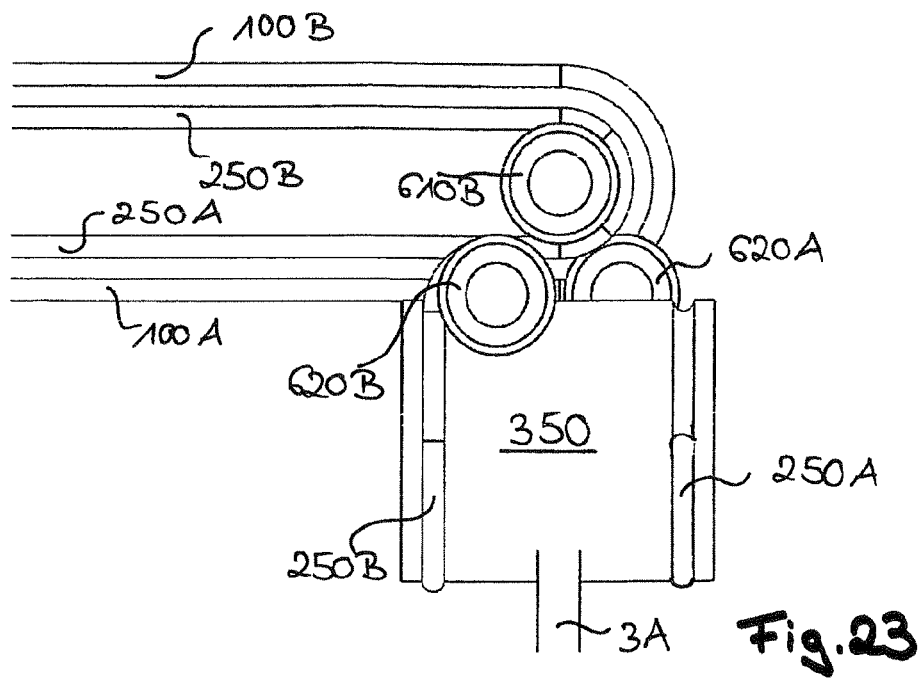
Figure 24:
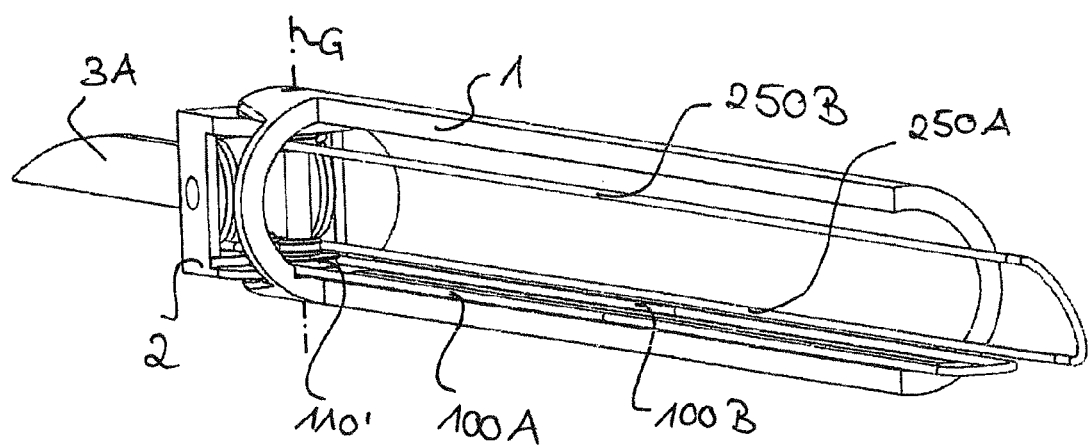
Figure 25:
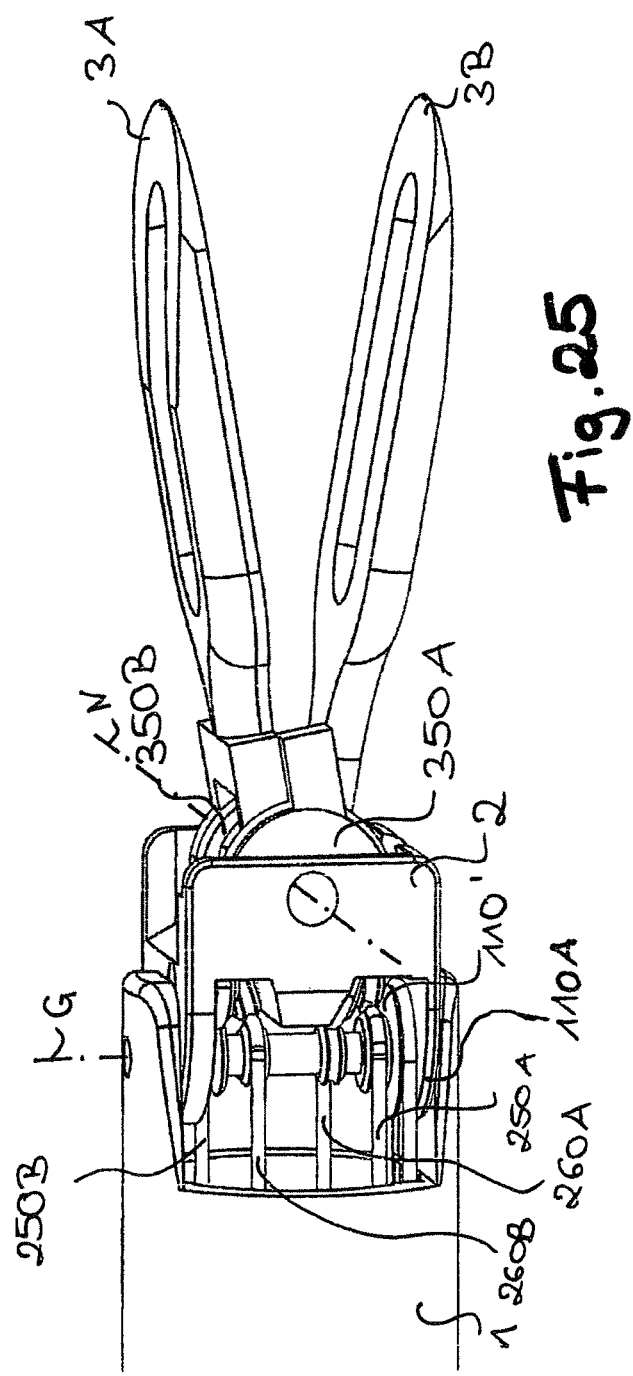
Figure 26:
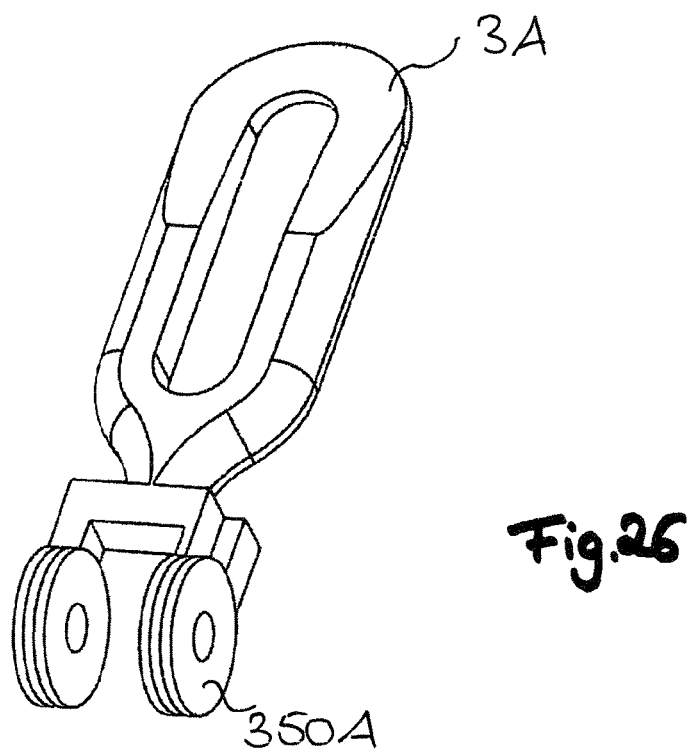
Figure 27:
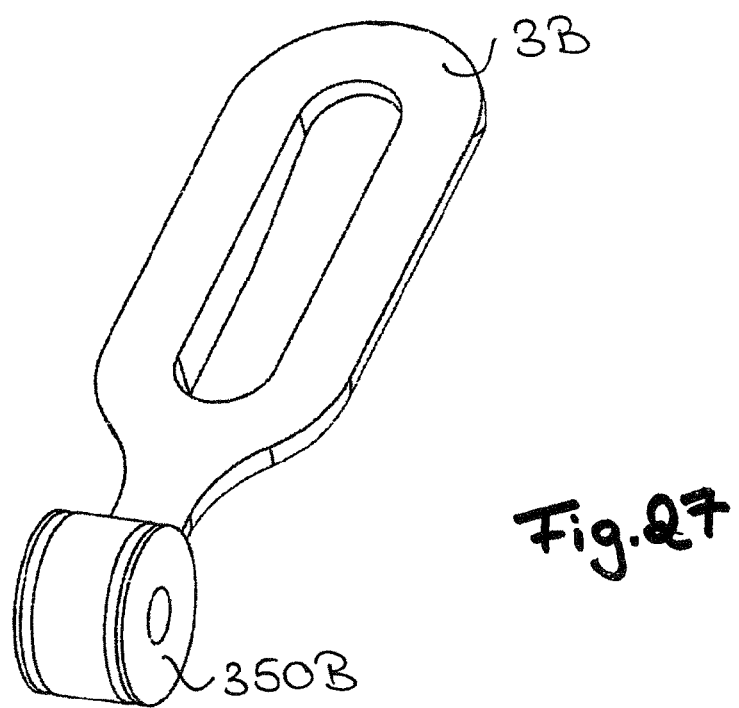
Figure 28:
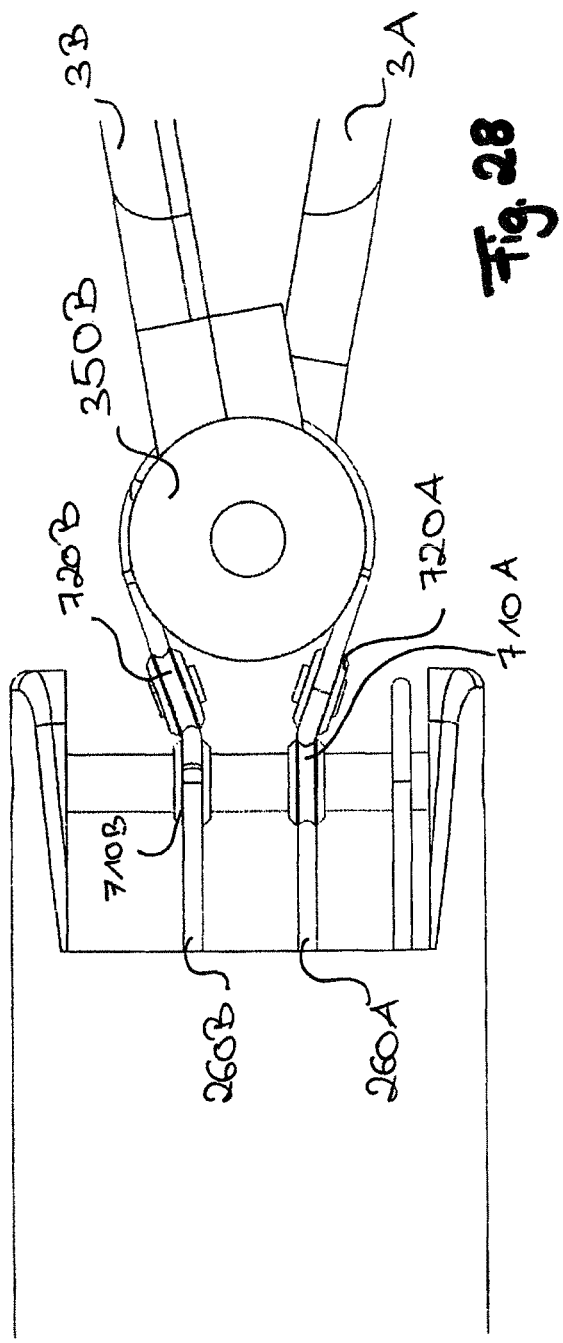
Figure 29:
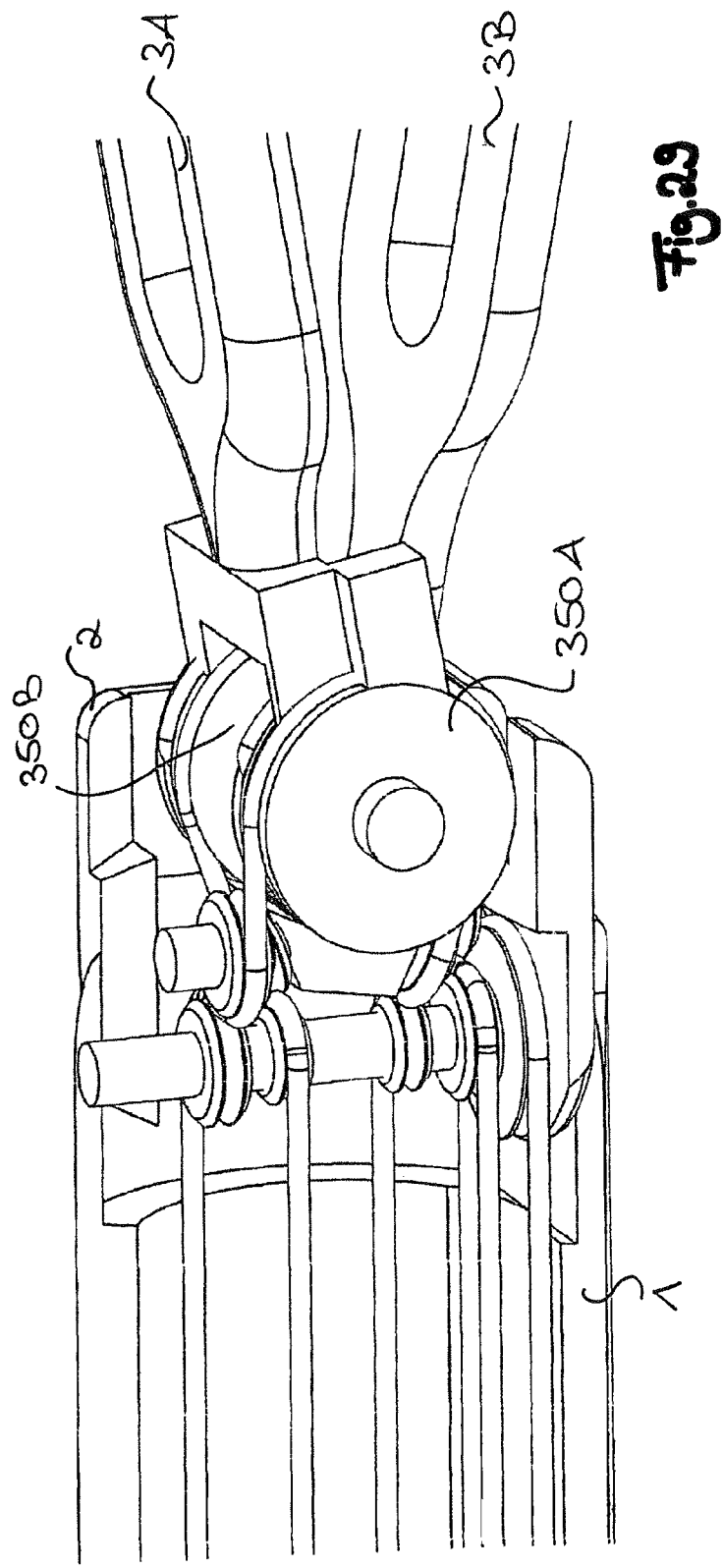
Figure 30:
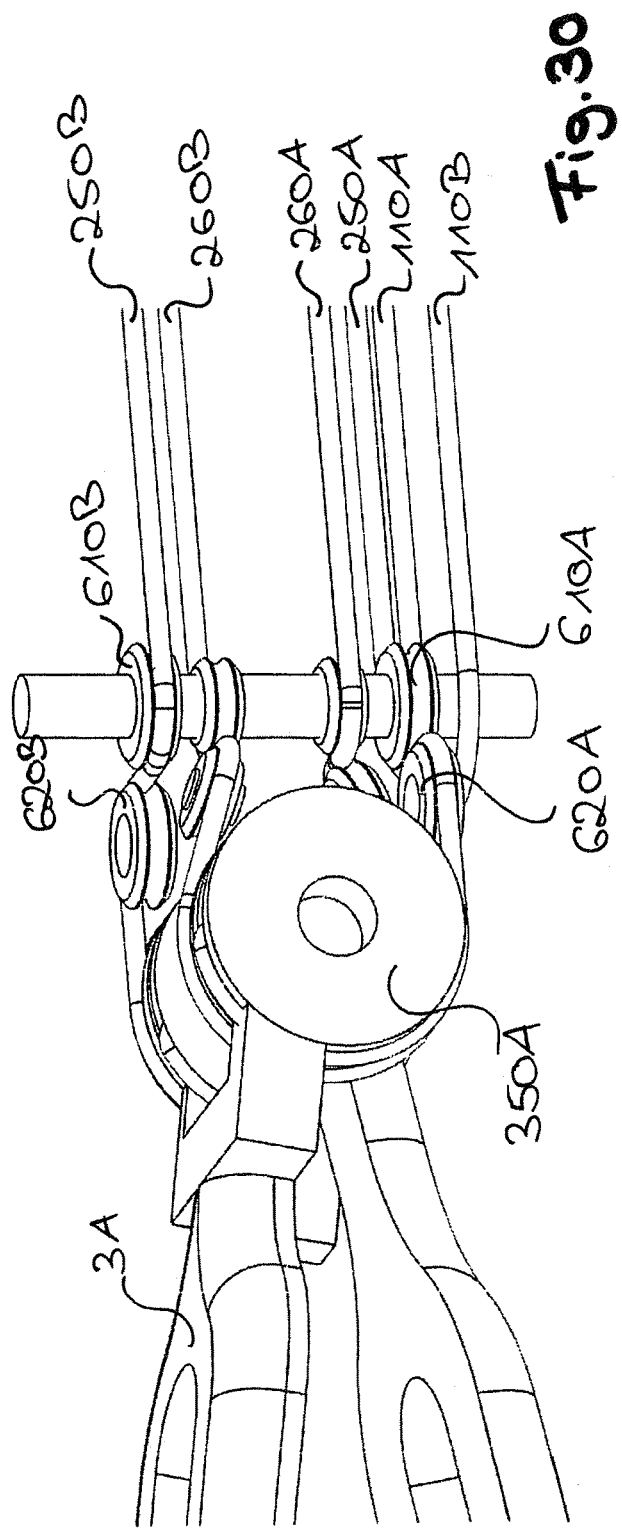
Figure 31:
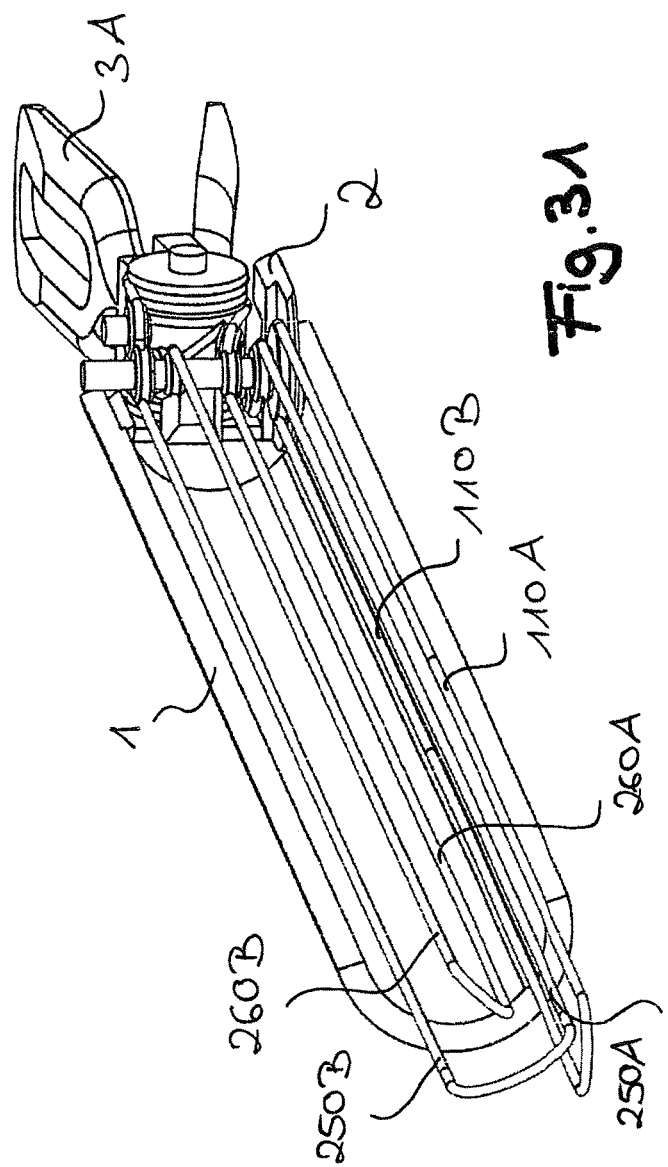
Figure 32:
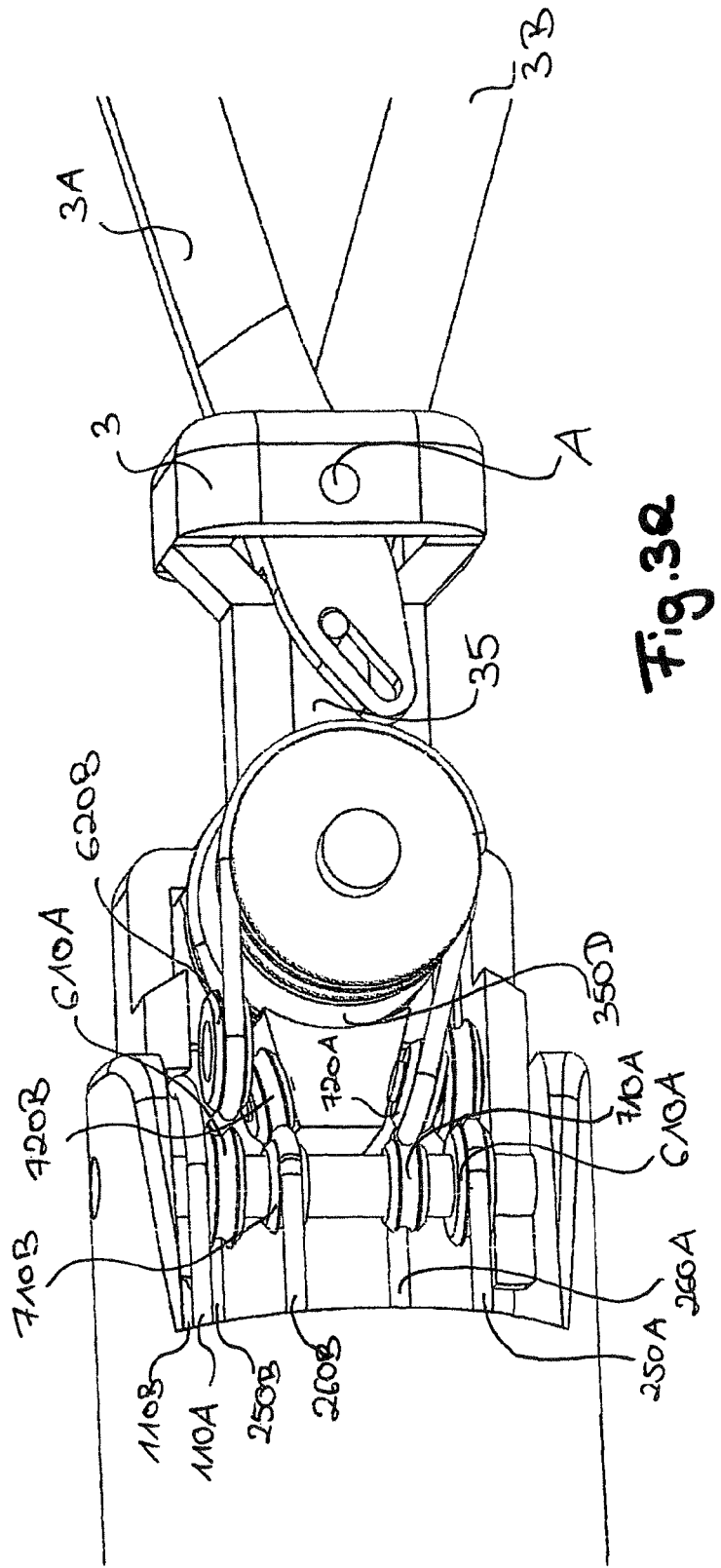
Figure 33:
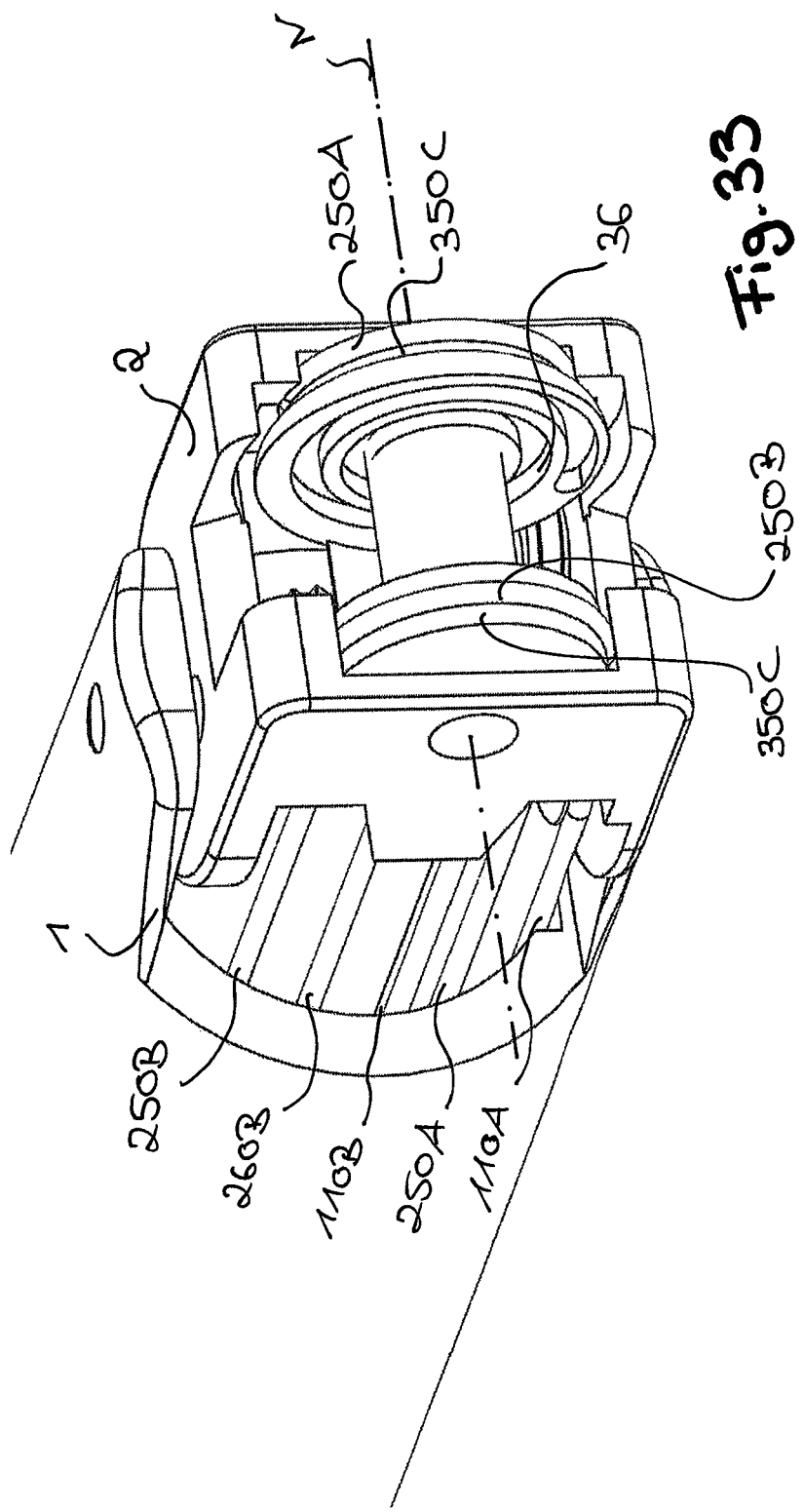
Figure 34:
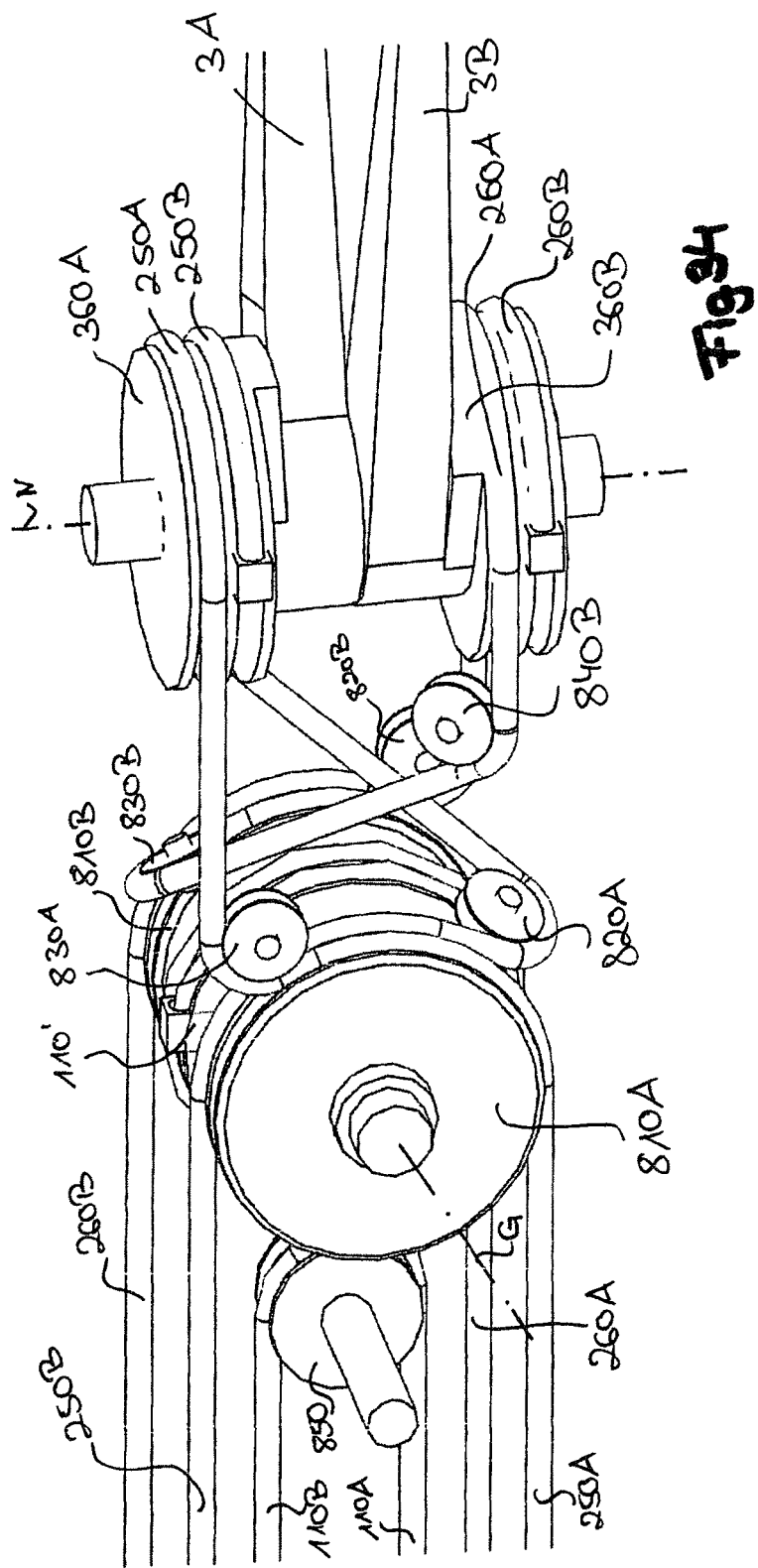
Figure 35:
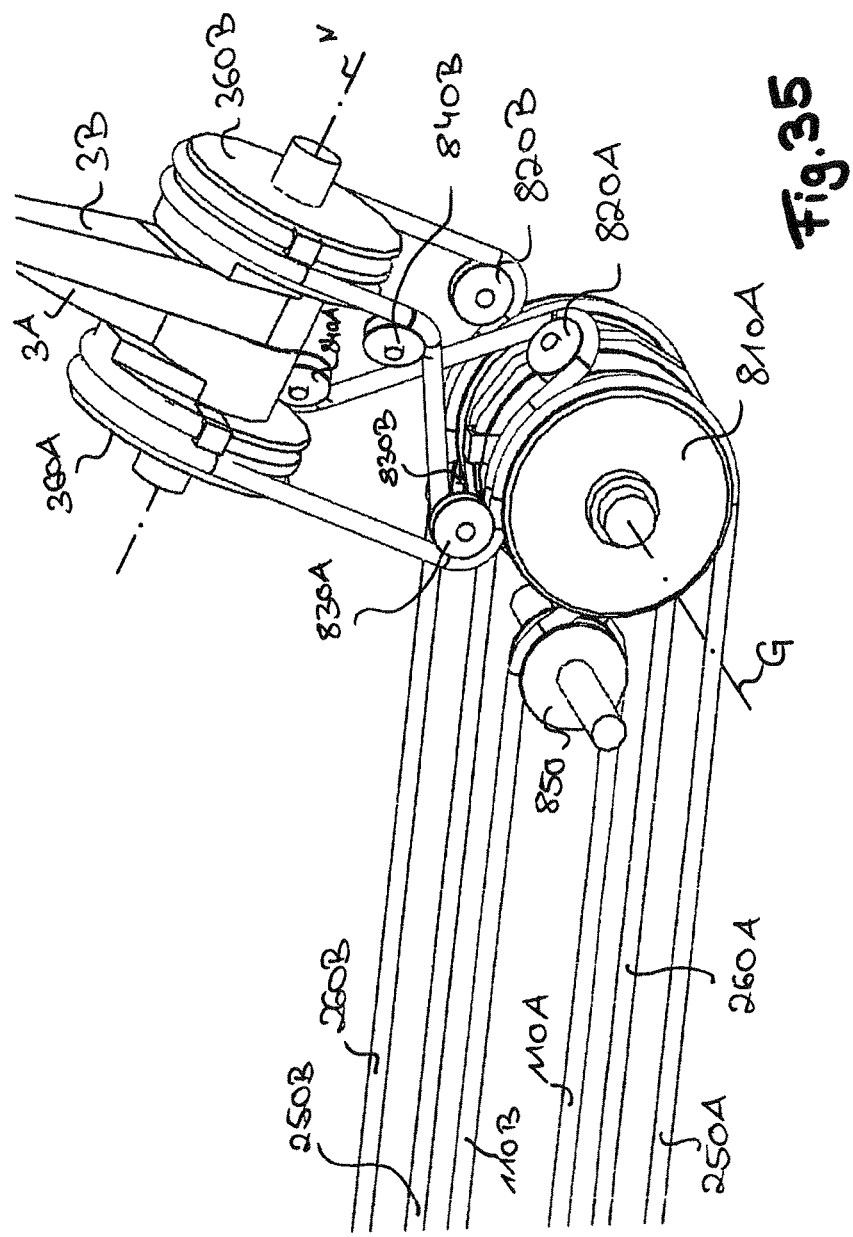

Further advantages and characteristics can be derived from the dependent claims and the embodiment examples. For this, the drawings show, in part schematically:

FIG. 1: a part of a surgical instrument according to a first design of the present invention in a perspective view;

FIG. 2: a variation on the surgical instrument according to FIG. 1;

FIG. 3: the surgical instrument according to FIG. 2, viewed in another perspective;

FIG. 4: a variation on the surgical instrument according to FIG. 2, viewed in a perspective corresponding to FIG. 3;

FIG. 5: a part of a surgical instrument according to a second design of the present invention, in a perspective view;

FIG. 6: the surgical instrument according to FIG. 5, without a tool holder;

FIG. 7: a part of a surgical instrument according to a third design of the present invention, in a perspective view;

FIG. 8: the surgical instrument according to FIG. 7, with a transparent tool holder;

FIG. 9: an assembly of the surgical instrument according to FIG. 7, in a perspective view;

FIG. 10: a conversion transmission of the assembly according to FIG. 9;

FIG. 11: a tool base body of the assembly according to FIG. 9;

FIG. 12A/12B: two levers of the assembly according to FIG. 9 in a closed/spread position;

FIG. 13: a part of a surgical instrument according to a fourth design of the present invention, in a perspective view;

FIG. 14: the surgical instrument according to FIG. 13, from the opposite side;

FIG. 15: a part of a surgical instrument according to a fifth design of the present invention, in a perspective view;

FIG. 16: two wraparound transmissions of the surgical instrument according to FIG. 15;

FIG. 17: a form-locking traction means, acting together with a wheel, in a surgical instrument according to one design of the present invention, in a top view;

FIG. 18: a variation on the design in FIG. 17, in a perspective view;

FIG. 19: a part of a surgical instrument according to on design of the present invention, in a perspective view;

FIG. 20: a form-locking pushing means, acting together with a wheel, of the surgical instrument according to FIG. 19;

FIG. 21: a part of a surgical instrument according to a sixth design of the present invention, in a perspective view;

FIG. 22: a further view of the surgical instrument according to FIG. 21, wherein components are omitted;

FIG. 23: a part of the surgical instrument according to FIG. 21, in a top view, in an angled position;

FIG. 24: the surgical instrument according to FIG. 21, in another perspective view, with a cut-off shaft end;

FIG. 25: a part of a surgical instrument according to a seventh design of the present invention, in a perspective view;

FIG. 26: a tool base body with a base lever of the surgical instrument according to FIG. 25, in a perspective view;

FIG. 27: a further lever with a further output drive wheel of the surgical instrument according to FIG. 25, in a perspective view;

FIG. 28: a part of the surgical instrument according to FIG. 25, in a side view;

FIG. 29: the surgical instrument according to FIG. 25, in another perspective view, with a cut-open tool holder and shaft end;

FIG. 30: a part of the surgical instrument according to FIG. 25, in another perspective view;

FIG. 31: the surgical instrument according to FIG. 25, in another perspective view, with a cut-open shaft end;

FIG. 32: a part of a surgical instrument according to an eighth design of the present invention, in a perspective view, with a cut-open tool holder;

FIG. 33: a part of the surgical instrument according to FIG. 32;

FIG. 34: a part of a surgical instrument according to a ninth design of the present invention in a perspective view, in a neutral yaw position; and FIG. 35: the part of the surgical instrument according to FIG. 34, in an angled yaw position.

FIG. 1 shows the distal part of a surgical instrument according to a first design of the present invention, in a perspective view, with a shaft end 1. This can be connected to the further, not depicted, hollow cylindrical shaft, or be mounted on said shaft, in an articulated manner, in particular about a longitudinal axis of the shaft, in a rotatable manner, in order to represent a degree of freedom, which is not explained further in the following, in particular, a rolling of the tool about a rolling axis (horizontal in FIG. 1). The shaft can be permanently or releasably connected, likewise not depicted, to a robot, which can spatially position the instrument as a whole.

A tool holder 2 is rotatably mounted in the shaft end 1, such that it can rotate about a yaw axis G. A drive wheel, which is not visible in FIG. 1 (cf. FIG. 2: 110), which shall also be referred to in the following as the tool holder wheel, is connected in a rotationally fixed manner to the tool holder 2, and in particular, is designed as an integral part thereof, for example, is cast thereto, and is encircled by a toothed or frictional belt having two strands 100A', 100B' in a form- or friction-locking manner. These belts 100' form a drive means, in particular a traction means, by means of which the tool holder 2 can be rotated about the yaw axis G, in that a traction strand is drawn away from the tool holder, and the opposite traction strand, integrally connected thereto, is guided correspondingly.

A tool 3 is mounted in the tool holder 2, exhibiting a base lever 3A and a worm wheel 30, rigidly connected thereto, so as to be rotatable about a pitch axis N. A worm 31 meshes with the worm wheel 30, wherein the worm is mounted in the tool holder 2, such that it can rotate about the yaw axis G. The worm 31 is rigidly connected to an intermediate wheel, which is not visible in FIG. 1 (cf. FIG. 2: 210), which is actuated, as is the case with the tool holder wheel, by a toothed or friction belt 200' in a form- or friction-locking manner, and for this purpose is partially encircled by said belt. This belt 200' forms a drive means, in particular a traction means, by means of which the worm 31 can rotate about the yaw axis G, in that a traction strand is pulled away from the tool holder 2, and the opposite traction strand, integrally connected thereto, is guided correspondingly.

The worm 31 and the worm wheel 30 form a gear transmission, wherein the worm 31 forms a drive wheel, which is mounted on the tool holder 2 so as to be able to rotate about an input transmission axis that is flush with, or identical to, the yaw axis G, and wherein the worm wheel 30 forms an output drive wheel, which is mounted on the tool holder 2 so as to be able to rotate about an output transmission axis that is flush, or identical to, the pitch axis N, by means of which the tool 3 can rotate about the pitch axis N, and which is connected to the drive wheel 31 in a form-locking manner, in that it meshes with said drive wheel. One sees that the range of rotation about the yaw and pitch axes is, in each case, greater than 180°, or +90° respectively. In addition, it is apparent that the movements about the yaw and pitch axes are independent of one another. The friction occurring in the system results from the bearing and transmission friction, and can be readily modulated, which enables contact or reaction forces to be transmitted to the base lever 3A from the drive forces in the drive means 100A', 100B', 200', based on a dynamic model.

FIG. 2 shows a distal part of a surgical instrument according to a variation on the first design for the present invention, in a perspective view. Components corresponding to one another are provided with the same reference symbols, individualized, if applicable, by leaving out the apostrophe ('), such that in the following, explanations will only be given for the differences from the first design according to FIG. 1, while the variation, otherwise, corresponds to the first design according to FIG. 1.

In the variation according to FIG. 2, the belts are replaced by cords 100, or 200, respectively, which form a drive means, having two cord strands 100A, 100B, or 200A, 200B, respectively, integrally connected to one another (cf. FIGS. 3, 4), which encircle, in part, the tool holder wheel 110, or intermediate wheel 210, respectively, in a friction-locking manner and/or are connected thereto in a form- or force-locking manner. For guiding the cord and, if applicable, for increasing the friction, the wheels 110, 210 exhibit corresponding guide grooves on their circumference.

FIG. 3 shows the surgical instrument according to FIG. 2, in a perspective view, seen from drives (not shown). These can be permanently or releasably connected, for example, to the shaft or the robot guiding said shaft.

One sees the two traction strands 100A, 100B of the cord 100 for rotating the tool holder 2 about the yaw axis G and the two traction strands 200A, 200B of the cord 200 for rotating the tool 3 about the pitch axis N via the intermediate wheel 210 and the worm gear transmission 30, 31.

The input drive side (front in FIG. 3) ends of the traction strands 100A, 100B, 200A, or 200B, respectively, are each attached to levers, for example, rotated synchronously by an electric motor in opposing directions, about an axis of rotation parallel to the yaw axis G, such that in each case, one traction strand is drawn away from the tool holder, and the other traction strand is guided toward the tool holder, in order to rotate the tool holder wheel 110, or the intermediate wheel 210, respectively, and via said wheels, the worm 31. Likewise, the two input drive side ends of a traction strand pair can also, for example, be drawn in and let out by means of linear motors.

FIG. 4 shows a variation on the surgical instrument according to FIG. 2, in a view corresponding to FIG. 3. Components corresponding to one another are provided with the same reference symbols, such that in the following, explanations shall only be given with respect to the differences to the design according to FIG. 3, while the variation otherwise corresponds to the design according to FIG. 2.

In the variation, the two traction strand pairs 100A and 100B, or 200A and 200B, respectively, are each also connected at their input drive side ends (front in FIG. 4) to one another, designed, for example, to be integral with one another. The (not depicted) drives drive said traction strand pairs by means of intermediate wheels 190, or 290, respectively, which each form, together with the traction cords 100, or 200, respectively, and the intermediate wheel 210, a drive means for rotating the drive wheel 110 or 31, respectively. The traction cords 100, 200 each form a closed loop and each encircle the intermediate wheels 190, or 290, respectively, and the tool holder wheel 110, or the intermediate wheel 210, over 180°.

FIG. 5 shows a part of a surgical instrument according to a second design of the present invention, in a perspective view, and FIG. 6 shows the distal ends thereof, wherein, for purposes of clarification, the tool holder is omitted. Components corresponding to one another are provided with the same, or mutually corresponding reference symbols, such that in the following, explanations will only be provided for the differences with respect to the first design, or the variations thereof, respectively, according to FIGS. 1-4, while the second design otherwise corresponds thereto. As with all designs, a further rotational axis can also be provided here in the proximal, not depicted, region of the shaft end 1, which enables a rotation about the shaft axis. The drive means can be decoupled from this rotation, or be coupled to this rotation.

In the second design, the tool exhibits, aside from the base lever 3A, a further lever 3B, having a construction that is mirror symmetrical to the base lever 3A, representing a second blade of a scissors or forceps type tool. Accordingly, the further lever 3B is also rigidly connected to another worm wheel 30B, which is mounted in the tool holder 2 so as to be rotatable about the pitch axis N. A further worm 31B meshes with the further worm wheel 30B, which is mounted in the tool holder 2 so as to be rotatable about a further input transmission axis. The further worm 31B is rigidly connected to a further intermediate wheel 320, which can be seen in FIG. 6, which is designed as a gearwheel, as is the case with an intermediate wheel 220, rigidly connected to the worm 31A.

The further worm 31B and the further worm wheel 30B form a further gear transmission, wherein the further worm 31B forms a further drive wheel, which is mounted on the tool holder so as to be rotatable about an input transmission axis, offset parallel to the yaw axis G, and wherein the further worm wheel 30B forms a further output drive wheel, which is mounted on the tool holder 2 so as to be rotatable about a further output transmission axis, which is flush with, or identical to, the pitch axis N, by means of which the further lever 3B can rotate about the pitch axis N, and which is connected to the further drive wheel 31B in a form-locking manner, in that it meshes therewith.

The two worms 31A, 31B, which are mounted in the tool holder 2 so as to be rotatable about input transmission axes disposed parallel to the yaw axis in a mirror symmetrical manner, and are each connected to a gear wheel 220 or 320, respectively, are rotated via the traction means 200 or 300, respectively. For this, they each encircle an intermediate wheel 210 or 310, respectively, having a small diameter, which is rigidly connected in a recess-fitted manner to an intermediate wheel 215 or 315, respectively, designed as a gear wheel, having a larger diameter, which in turn meshes with the gear wheel 220 or 320, respectively. In this manner, the two closed traction means 200, 300 can be guided in the hollow shaft parallel to the traction means 100. They form, together with the intermediate wheels 210, 310, having the smaller diameter, which they encircle over 180°, the gear wheels 215, 315, designed so as to be integral therewith in a recess-fitting manner, and the intermediate, or gear, wheels 220, 320 that mesh therewith, as well as, if applicable, the intermediate wheels 290 (cf. FIG. 4), in each case a drive means for driving the drive wheels or worms, 31A, 31B, respectively of the tool drive or further wheel drive, respectively. The two drive means, on one hand, as well as the base and further levers 3A, 3B, and the tool or further wheel drives, respectively, on the other hand, are designed to be mirror symmetrical on planes rotated by 90°. In particular, the tool holder wheel 110 is disposed centrally between the two intermediate wheels 210, 310, which in turn are disposed within the two gear wheels 215, 315, and mesh with intermediate wheels 220 or 320, respectively, accordingly disposed on opposite sides of the tool holder.

The second design can offer the same advantages as the first embodiment, whereby, in the second embodiment, the symmetrical branching of the drive means 200, 300, guided parallel to the drive means 100, represents a particularly favorable kinematics.

FIG. 7 shows a part of a surgical instrument according to a third design of the present invention, in a perspective view, and FIG. 8 shows the distal ends thereof, from the opposite side, whereby the tool holder is depicted as transparent for reasons of clarity. Components corresponding to one another are provided with the same, or with corresponding reference symbols, such that in the following, explanations shall only be provided regarding the differences to the first or second designs and their variations, in accordance with FIGS. 1-6, while the third design otherwise corresponds thereto.

Figure 12B:
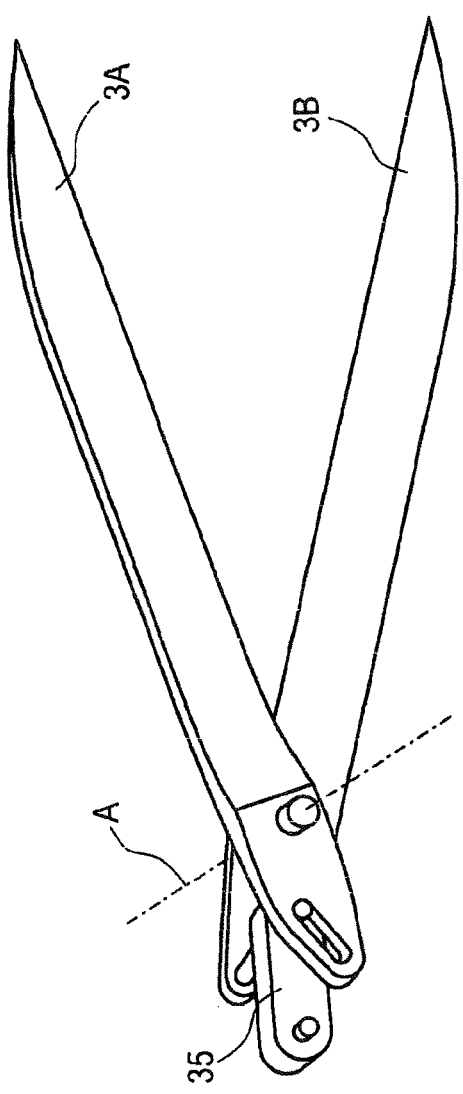

In the third embodiment, the tool exhibits a tool base body 3, which is depicted alone in FIG. 11. Two levers 3A, 3B, which can be spread apart in a symmetrical manner, are mounted in this base body, so as to be rotatable about a tool axis A, as is shown, in particular, in FIG. 9. The two levers 3A, 3B, as is clear from the figure sequence of FIGS. 12A, 12B, are connected to one another in the manner of a scissors or forceps, and exhibit link guides on their surfaces opposite the blades (left in FIG. 12) running in opposite directions, in which pins are guided in a form-fitting manner, so as to be displaceable, which protrude from opposite surfaces of a sliding body 35. One sees that a translational motion of the sliding body 35 toward the tool axis A, or away therefrom, respectively, spreads or closes, respectively, the levers or blades 3A, 3B.

For this, the sliding body 35 is guided in a longitudinal groove 37, particularly visible in FIG. 11, such that it can be displaced in a translational manner, which is formed in the tool base body 3. On the surface facing away from the tool axis A, the sliding body 35 exhibits another pin, which is guided in a form-fitting manner in a groove in the form of an Archimedean spiral 36. This link guide converts, in a known manner, a rotation of the wheel 30C provided by the spiral 36, into a translation of the sliding body 35, which in turn forcibly actuates a rotation of the levers 3A, 3B about their tool axis A. In this manner, these components function as conversion transmissions for mutually converting rotational and a translational motions.

The wheel 30C is, as can be seen in particular in FIG. 9, designed as a further worm wheel, which is actuated by the further worm 31C, while the tool holder base body 3 is rigidly connected to a worm wheel 30A, which is actuated by the worm 31A. Between the two worm wheels 30A, 30C, the two gear transmissions and the drives actuating them, the third design corresponds to the second design, as is clear from FIG. 8. In contrast to the second design, however, the levers 3A, 3B rotate with an actuation of the further gear transmission 30C, 31C, due to the conversion transmissions 35, 36, about the tool axes A, which are offset in parallel with respect to the pitch axis N. The tool as a whole, in particular its base body 3, is rotated, however, by means of the tool-gear transmissions 30A, 31A about the pitch axis N. The opening or closing of the levers 3A, 3B results in the embodiment example based on the size and conversion ratios thereof in the tool- and further gear transmissions, proportional to the difference of the rotation of the worms 31A, 31C about their parallel input transmission axes, which additionally, are offset, parallel to the yaw axis G, in a symmetrical manner. In order, for example, to retain the levers in the same open position during a pitch movement of the tool 3, the traction means 200 and 300 are activated in a synchronous manner.

FIG. 13 shows a part of a surgical instrument according to a fourth design of the present invention, in a perspective view, and FIG. 14 shows the distal ends thereof, from the opposite side. Components corresponding to one another are provided with the same or corresponding reference symbols, such that in the following, explanations shall be provided only for the differences to the first, second or third designs and their variations in accordance with FIGS. 1-12, while the fourth design otherwise corresponds to these. As explained above, a further axis of rotation may be provided in the proximal region of the shaft end 1, which enables a rotation about the shaft axis, from, or to, which the drive means can be decoupled or coupled, respectively.

The assembly of the tool corresponds substantially to the third design, whereby, in the fourth design, the worm 31A of the tool-gear transmission is not offset parallel to the yaw axis G, but is flush therewith. The other gear transmission 30C, 31C is designed in the fourth design as a crown gear transmission, wherein the output drive, or crown gear 30C, spreads or closes, respectively, the levers 3A, 3B by means of an Archimedean spiral (not visible in FIGS. 13, 14), as has been explained in reference to the FIGS. 9-12.

A traction means 300 encircles an intermediate wheel 310 in the fourth design as well, which is rigidly connected to an intermediate wheel 315', having the same diameter in the embodiment example, and is functionally connected to an intermediate wheel 320', which is rigidly connected to the drive wheel, or crown gear wheel 31C of the further gear transmission. In contrast to the third embodiment example, the two functionally connected intermediate wheels 315', 320' are not, however, designed as intermeshing gear wheels, but rather, are functionally connected by means of a closed traction means, in particular, a cord 317 of a wraparound transmission. In addition, in the fourth design, the tool holder wheel 110 is disposed on the edge of the tool holder 2, such that the worm 31 and the intermediate wheel 210, which is flush therewith and connected thereto in a rotationally fixed manner, and is encircled by a traction means 200, is disposed in this case between the drive means 100 for actuating the tool-gear transmission and the drive means 300 for actuating the other gear transmissions 30C, 31C.

FIG. 15 shows a part of a surgical instrument according to a fifth design of the present invention, in a perspective view, and FIG. 16 shows two wraparound transmissions of this surgical instrument. Components corresponding to one another are provided with the same or corresponding reference symbols, such that in the following, explanations shall be given only for the differences to the first, second, third or fourth designs and their variations in accordance with FIGS. 1-14, while the fifth design otherwise corresponds to these. As explained above, a further axis of rotation can be provided in the proximal region of the shaft end 1, which enables a rotation about the shaft axis from, or to, which the drive means can be decoupled or coupled, respectively.

In the fifth design, particularly in comparison with the second design, instead of the gear transmission, two symmetrically structured wraparound transmissions are provided for rotating the two levers 3A, 3B about the pitch axis N.

One of these two structurally identical wraparound transmissions, which in the following shall be referred to as the tool-wraparound transmissions, without imposing any limitation to the generality, exhibits a drive wheel 213 rotatably mounted on the tool holder 2, which is encircled by a traction means 200 of a drive means, and via corresponding counter-movements of its two traction strands, can be rotated about an input transmission axis, which is flush with the yaw axis G in the present example.

Two traction strands 400A, 400B, connected to a closed loop, twisted about 180° and integral to one another, which differ to this traction means 200, encircle both the drive wheel 213 as well as an output drive wheel 325A, which is mounted on the tool holder 2 so as to be rotatable about an output transmission axis, which is flush with the pitch axis N in the present example, and is rigidly connected to the base lever 3A, in particular, is designed as an integral part thereof, in order to couple the input and output drive wheels 213, 325A.

For this, the one traction strand 400A (above in FIG. 16) runs away from the drive wheel 213 at a right angle to the yaw axis G, and from there toward the output drive wheel 325A, substantially without a change in direction, at a right angle to the pitch axis N, from where the traction means encircles this output wheel 325A over 180°, and from there, in turn, runs at a right angle to the pitch axis N. Here, the other traction strand 400B runs via a first guide wheel 410A to a second guide wheel 410B, from where the closed traction cord 400 again runs toward the drive wheel 214 at a right angle to the yaw axis G, and encircles said drive wheel over 180°. The traction strands can be connected to the output wheel in a form- and/or force-locking manner. The other traction strand 400B forms an angle of approx. 45° to both the yaw and pitch axes G, N between the first and second guide wheels 410A, 410B. Accordingly, the axes of rotation for the two guide wheels 410A, 410B are tilted against both the yaw and pitch axes G, N, at approx. 45°.

Through rotating the drive wheel 213 by means of the traction means 200, the output drive wheel 326A and the base lever 3A are pivoted or rotated together about the pitch axis N via the wraparound transmission with the traction strands 400A, 400B. In an analogous manner, independently thereof, the other lever 3B can also be pivoted about the pitch axis N, when the other drive wheel 313 of the other wraparound transmission is rotated by means of the other drive means 300. Here as well, two traction strands 500A, 500B, integrally connected to one another, and differing from the other drive means 300, encircle the other input and output drive wheels 313, 325B, whereby, in turn, a traction strand 500A runs substantially at a right angle to the yaw and pitch axes G, N, while the other traction strand 500B forms an angle of approx. 45° to both the yaw and pitch axes G, N between accordingly tilted guide wheels 510A, 510B.

Similar to in the second and third designs, with the fifth design as well, a tool retainer wheel 110 is disposed between the two output drive wheels 213, 313, and rigidly connected to the tool holder 2. This is driven by means of a flat belt 100', as can be seen in FIG. 15, which shows in an exemplary manner that in general, cord and belt traction means can both be implemented in one design in accordance with the invention. The embodiment example also shows in an exemplary manner that in general, in accordance with the invention, a tool- and a further wraparound transmission according to the second aspect of the present invention, can preferably be disposed such that they are mirror symmetrical to one another.

As with the previously explained designs, advantageous kinematics and dynamics can also be obtained with this fifth design. In particular, the traction means 400, 500 of the wraparound transmission, differing from the drive means-traction means, which in turn, can be designed as, preferably closed, cord, cable, toothed, or friction belt traction means, for example, enabling a simple modeling of the friction and thus an indirect, model based detection of forces to the levers 3A, 3B based on the forces in the drive means. Because, substantially, only one ratio, corresponding to the diameter ratios of the drive wheels 213, 313 to the output drive wheels 325A, 325B, is contained in the transmissions for the drive of the levers 3A, 3B, it is possible, in an advantageous manner, to determine to a large degree the torques applied to the levers 3A, 3B by measuring the forces or torques applied to the drive.

In the preceding embodiments, for the most part traction means functioning together with input, output, or intermediate wheels in a friction-locking manner are shown. In a variation, a traction means of a drive means and/or a wraparound transmission can also act together with a corresponding wheel in a form-locking manner, additionally or alternatively thereto. FIG. 17 shows, in an exemplary manner, for this purpose, a wheel R, which is encircled by a traction means Z. The wheel can, for example, be one of the wheels 110, 190, 210, 213, 290, 310, 313, 315', 320', 324A, or 325B, and accordingly, the traction means can be one of the traction means 100, 200, 300, 317, 400 or 500 (A, B). A lug is formed in the traction means Z, which is integrated in a corresponding slot in the wheel R, such that the traction means Z is rigidly attached to the wheel R in a form-locking manner. This can advantageously reduce or prevent frictionally caused wear and/or micro-slippage, which are both equally undesirable in surgical instruments.

FIG. 18 shows, in an exemplary manner, the other variation, in which two output drive-side unconnected traction strands ZA, ZB, i.e. by means of a wheel R', are each connected at their ends to the wheel R'. The two traction strands ZA, ZB run on opposite sides of the wheel R' therefrom, such that, in turn, a pulling movement of a traction strand causes an opposite movement of the other traction strand and a rotation of the driven wheel R'. In the zero, or neutral position of the driven wheel R', shown in FIG. 18, a wrapping between the attachment and the run-out of a traction strand amounts to approx. 270° in each case, such that the wheel R' can be rotated from the zero position by means of a traction strand by more than 90°, until it is fully run out. The wheel R' can, in turn, be one of the wheels 110, 190, 210, 213, 290, 310, 313, 315', 320', 325A or 325B, in particular, and the traction means ZA, ZB, accordingly, can be one of the traction means 100, 200, 300, 317, 400, or 500 (A, B).

In the preceding embodiment examples, traction means are shown substantially. In a variation, instead of a traction means having two traction strands, a pushing means can also be used, in particular, a push rod. FIG. 19 shows, for this purpose, in an exemplary manner, a variation in accordance therewith, of the third embodiment example according to FIG. 6, to the description of which, reference is made here. There, the intermediate wheels 110, 210 and 310 of the drive means 100, 200, or 300, respectively, are each encompassed by traction cords in a friction-locking manner.

In the variation on FIG. 19, in contrast, a slit is formed in the radial direction in each of the intermediate wheels 110', 210' and 310', which are rigidly connected to the tool holder 2, or the intermediate wheels 215, 315, respectively, in each of which a sliding body (see FIG. 20) is guided in a form-fitting manner, such that it can be displaced in a translational manner. A push rod 100', 200' or 300', respectively, is attached to each of these in an articulated manner. As can be seen, in particular from the top view in FIG. 20, a translational displacement of the push rod 100', for example, causes a corresponding rotation of the intermediate wheel 110', such that this can also be actuated by one push rod 100', which preferably is guided such that it can be displaced in a direction, in particular, parallel to the longitudinal axis of the shaft, in a translational manner, instead of by means of two traction strands running in opposite directions. In particular, one of the wheels 110, 190, 210, 213, 313, 315', 320', 325A or 325B, can also, in a variation that is not depicted, be actuated in a corresponding manner by a push rod. Additionally or alternatively, it is possible to attach a push rod in an articulated manner to the driven wheel itself, instead of to a sliding body. This can then be attached in an articulated manner, for example, at opposite ends to a crankshaft of a drive.

FIG. 21 shows a part of a surgical instrument according to a sixth design of the present invention, in a perspective view, FIG. 22 shows another view, whereby, for purposes of clarity, the shaft end and tool holder, in particular, are omitted, FIG. 23 shows a differential transmission of this surgical instrument, without this supporting tool holder, for purposes of clarity, and FIG. 24 shows this from another perspective view from the back, i.e. from a side facing away from the tool, whereby, for clarity, the shaft end, in particular, is cut off. Components corresponding to one another are provided with the same or corresponding reference symbols, such that in the following, explanations shall only be provided for the differences to the preceding designs or their variations, while reference is made otherwise to their descriptions. In particular, a further axis of rotation may be provided in the proximal region of the shaft end 1, which enables a rotation about the shaft axis, from, or to, which the drive means can be decoupled or coupled, respectively.

In the sixth design, the surgical instrument exhibits a shaft end 1, as is the case with the first design, or its variations, on which a tool holder 2 is rotatably mounted, such that is can rotate about the yaw axis G. A tool holder wheel 110' is connected in a rotatably fixed manner to the tool holder 2, and is encircled by two traction strands 100A, 100B, integrally connected to one another, which form another, or further drive means, by means of which the tool holder 2 can be rotated about the yaw axis G, in that a traction strand is drawn away from the tool holder and thus guided toward the opposite traction strand integrally connected thereto, in a corresponding manner (cf. FIG. 24 and the description of the first design).

A tool is contained in the tool holder 2, which exhibits a base lever 3A and an output drive wheel 350 rigidly connected thereto, which is mounted so as to be rotatable about a pitch axis N, which is flush with, or identical to, an output transmission axis of a (tool-) differential transmission.

As can be seen, in particular, in FIGS. 22, 23, the output drive wheel 350 exhibits two circumferential grooves disposed on each side of the yaw axis G, from which two traction strands 250A, 250B run in opposite directions.

The two traction strands 250A, 250B, as can be seen in FIG. 24, are integrally connected to one another on the side facing away from the tool, or at the input drive side, and are pulled in opposite directions by means of an intermediate wheel (not shown), actuated by means of a motor, as has already been explained, in particular in reference to FIG. 4.

Both traction strands 250A, 250B are attached to the output drive wheel 350 at their free, tool-side ends. For this, the free ends are inserted in radial holes in the output drive wheel 350 lying opposite one another, and crimped, welded or glued, for example, therein. In a zero position or neutral position of the tool 3 depicted in FIG. 21, in which the base lever thereof is oriented parallel to the longitudinal axis of the shaft end 1, the two traction strands 250A, 250B are guided in the circumferential grooves, starting from their free ends attached to the output drive wheel 350, in opposite directions on the output drive wheel 350, over approx. 180° in each case, and then run parallel to one another on both sides of the yaw axis, away therefrom, or toward it.

In order to bypass the yaw axis G, the traction strands 250A, 250B are guided by means of guide wheels 610A, 610B, 620A, or 620B, respectively. Two guide wheels 610A, 610B are mounted on the tool holder 2, spaced apart from one another axially, so as to be rotatable about a guidance rotational axis, which is flush with the yaw axis G, and two other guide wheels 620A, 620B are mounted on the tool holder 2 on both sides of the yaw axis G, so as to be rotatable about other guide rotational axes parallel thereto, which are offset to one another in a symmetrical manner in the direction of the pitch axis N, away from the yaw axis G.

In order to actuate the base lever 3A in FIG. 22 downward, or in FIG. 23 inward, in the plane of the drawing, respectively, the one traction strand 250A, which runs from the output drive wheel 350 substantially perpendicular to the yaw and pitch axes, and is displaced by means of the guide wheel 620A and the guide wheel 610A perpendicular to the yaw axis, and bridges the yaw axis, is pulled away from the tool (to the left in FIG. 22), and runs thereby away from the output drive wheel 350, whereby the other traction strand 250B is guided correspondingly, due to the connection facing away from the tool (cf. FIG. 24), displaced by means of the other guide wheel 620B and the guide wheel 610B, perpendicular to the yaw axis on the opposite side, and runs toward the output drive wheel 350. By means of an opposite movement of the traction strand 250B away from the tool, the base lever 3A is actuated in FIG. 22 in the opposite direction, upward, or in FIG. 23 out of the plane of the drawing, outward. A movement of the tool holder 2 about the yaw axis G can be compensated for by means of corresponding compensation movements by the traction strands 250A, 250B.

The traction strands 250A, 250B, (further) guide wheels 610A, 610B, 620A, 620B, and the output drive wheel 350 form a (tool-) differential transmission.

FIG. 25 shows a part of a surgical instrument according to a seventh design of the present invention, in a perspective view, FIGS. 26-28 and 30 each show a part thereof, FIG. 29 show the part with the shaft end and the tool holder cut off, for purposes of clarity, and FIG. 31 shows this in a perspective view from the back, i.e. a side facing away from the tool. Components corresponding to one another are provided with the same or corresponding reference symbols, such that in the following, explanations shall only be provided for the differences to the preceding designs or their variations, and otherwise, reference is made to the descriptions thereof. In particular, as explained above, a further axis of rotation can be provided in the proximal region of the shaft end 1, which enables a rotation about the shaft axis, from, or to, which the drive means can be decoupled or coupled, respectively.

In the seventh design, the tool exhibits, aside from the base lever 3A, and further lever 3B, which represents a second jaw of a forceps type tool, that is mirror symmetrically, structurally identical to the base lever 3A. Accordingly, the further lever 3B is rigidly connected to a further output drive wheel 350B, which is mounted on the tool holder 2 so as to be rotatable about the pitch axis N.

FIG. 26 shows the base lever 3A and output drive wheel 350A rigidly connected thereto. The assembly and actuation correspond—aside from the differences explained in the following—to the previously explained six designs, such that reference is made to their description. As described there, and in particular, is apparent from FIG. 30, the base lever 3A can be rotated about the pitch axis by means of counter-traction to one of the two traction strands 250A, 250B, which run in opposing directions toward the output drive wheel 350A on both sides of the yaw axis, toward or away from the output wheel, respectively, and bypass the yaw axis thereby in that they are displaced by means of the guide wheels 610A, 610B, 620A, 620B in opposite directions perpendicular to the yaw axis G.

The rotation of the tool holder 2 also occurs by means of a further drive means 110A, 110B in the form of a closed traction cord, which encircles the tool holder wheel 110' in a friction-locking manner, as explained above.

As the overview of the FIGS. 25-27 shows in particular, the further output drive wheel 350B can rotate on a shaft (not depicted in FIG. 26) of the coil-shaped output drive wheel 350A, which is inserted, after the inserting the further output drive wheel, between its flanges (left and right in FIG. 26), and is thus also rotatably mounted on the tool holder 2. Its assembly and its actuation likewise correspond—aside from the differences explained in the following—to the previously explained designs, such that reference is made to their description. As is described there, and is apparent from FIG. 28 in particular, the other lever 3B can be rotated about the pitch axis by means of counter-traction on one of the two traction strands 260A, 260B, which run thereby in opposing directions on both sides of the yaw axis G toward the output drive wheel 350B, or away from it, respectively.

In order to bypass the yaw axis G, this further differential transmission exhibits guide wheels 710A, 710B, which are mounted inside the guide wheels 610A, 610B in the tool holder 2, so as to be rotatable about the yaw axis G.

In order to displace the traction strands 260A, 260B in both the direction of the pitch axis N (perpendicular to the drawing plane in FIG. 28) and in the direction of the yaw axis G (upward or downward in FIG. 28), and thus allow them to run out, parallel to one another on both sides of the yaw axis G in the front surface circumferential grooves of the output drive wheel 350B, toward or away from the further output drive wheel, the further guide wheels 720A, 720B of the further guide rotation axes, which guide the traction strands 260A or 260B, are tilted against the yaw axis in opposing directions at equal angles. In this manner the traction strands 260A, or 260B, respectively, of the further differential transmission, as is clear in particular in FIG. 31, can be guided inside of the traction strands 250A, or 250B, respectively, of the tool-differential transmission, and also run out, on both sides of the yaw axis in opposing directions, toward the further output wheel 350B, or away therefrom, respectively.

It is also apparent in FIG. 31 that the axes of rotation of the actuators for actuating the traction strand pairs (100A, 100B), (250A, 250B) and (260A, 260B) are tilted toward one another, in each case, at 60°.

FIG. 32 shows, in particular, a tool base body 3 with an output drive wheel 350D, and FIG. 33 shows a tool holder 2 and a further output drive wheel 350C, mounted therein so as to be rotatable about the pitch axis, of a surgical instrument according to the eighth design of the present invention, in a perspective view. Components corresponding to one another are provided with the same, or corresponding, reference symbols, such that explanations shall only be provided for the differences to the preceding designs or their variations, and otherwise, reference is made to their descriptions.

The eighth design corresponds substantially to a combination of the previously explained third or fourth designs, respectively, together with the seventh design described above.

As with the third, or fourth design, respectively, the tool exhibits a tool base body 3 (cf. FIG. 32), in which two symmetrical levers 3A, 3B, which can be spread apart from one another, are rotatably mounted, and are connected to one another in the manner of scissors or forceps, respectively, and which exhibit link guides on their surfaces opposite the blades, which run in opposing directions, in which pins are guided in a form-fitting, sliding manner, which project from opposite surfaces of a sliding body.

The output drive wheel 350D, designed as an integral part of the tool base body 3, corresponds to the assembly and actuation of the further output drive wheel 350B (cf. FIG. 27), such that in this regard, reference is made to the description of the seventh design—through opposing tractions to the traction strands 260A, 260B, the output drive wheel 350D can be rotated about the pitch axis (cf. FIG. 32).

The further output drive wheel 350C is designed in the manner of a coil, wherein a spiral-shaped groove is formed on at least one inner surface, or on both inner surfaces facing each other, of the two coil flanges of the further output drive wheel 350C, in each case, in which a pin of a sliding body 35 (cf. FIG. 10) is guided, such that it can be slid in a form-fitting manner.

The further output drive wheel 350C corresponds to the output drive wheel 350A in terms of its assembly and actuation, such that also in this respect, reference is made to the description of the seventh design—through opposing tractions to the traction strands 250A, 250B, the further output drive wheel 350C can be rotated about the pitch axis (cf. FIG. 33).

This causes a scissors-like spreading of the two levers of the tool, as is explained in reference to the third and fourth designs, in particular in FIGS. 10, 11: the traction strands 250A, 250B run in opposing directions toward the two coil flanges of the further output drive wheel 350C, toward and away from the further output drive wheel, respectively, wherein they are guided by means of (additional) guide wheels (not shown, cf. FIG. 30) in order to bypass the pitch axis. This causes a rotation of the further output drive wheel 350C. By means of the pin, or the pins, respectively, of the sliding body, which is, or are, guided in a form-fitting manner such that they can slide in the spiral-shaped groove, or the facing spiral shaped grooves of the further output drive wheel 350C, this rotational motion is converted to a translational movement of the sliding body 35 (cf. FIG. 10), which causes the scissors-like spreading of the two levers of the tool.

FIG. 34 shows the differential transmission of a surgical instrument according to a ninth design of the present invention, in a perspective view, in a neutral yaw position, i.e. not rotated about the yaw axis G, and FIG. 35 shows the differential transmission in an angled yaw position, i.e. rotated about the yaw axis G. Components corresponding to one another are provided with the same, or corresponding, reference symbols, such that in the following, explanations shall only be provided for the differences to the preceding designs or their variations, while otherwise, reference is made to their description. In particular, as explained above, a further rotational axis can be provided in the proximal region of the shaft end 1, which enables a rotation about the shaft axis, from, or to, which the drive means can be decoupled or coupled, respectively.

The ninth design corresponds substantially to a modification of the previously explained seventh design, corresponding to the previously explained fifth design.

In the ninth design, the tool exhibits a base lever 3A, which is rigidly connected to an output drive wheel 360A, which exhibits two parallel grooves, from which, or to which, respectively, the traction strands 250A, 250B run in opposite directions on the same side of the yaw axis G (above in FIG. 34), which are each attached to the output drive wheel 360A in a form- or material-locking manner, tangentially in corresponding projections of the output drive wheel 360A in the embodiment example of FIG. 34. The traction strand 250A is subsequently guided by means of a further guide wheel 830A toward a groove of a guide wheel 810A, which is mounted in the tool holder (not shown) so as to be rotatable about the yaw axis G, and runs from there to a drive, as is described above in reference to the seventh design (cf. FIG. 31, for example). The traction strand 250B is guided by means of a further guide wheel 820A toward a parallel groove of the guide wheel 810A, and runs from this guide wheel toward the other side of the yaw axis G to the drive. The further guide wheels 820A, 830A form, together with the guide wheel 810A, a channel for guiding the traction strands 250A, 250B, in order to securely guide these on the guide wheel 810A, even in the case of yaw movements of the tool holder. The traction strand 250B forms an angle of between 15° and 75° to the yaw and pitch axes, between them.

The base lever 3A exhibits a shaft, on which a further output drive wheel 360B is mounted, which is rigidly connected to another lever 3B, so as to be rotatable about the pitch axis. Its actuation corresponds to the actuation of the base lever 3A, or the output drive wheel 360A, respectively, explained above: the traction strands 260A, 260B run in opposing directions toward the other side of the yaw axis G (below in FIG. 34) on two parallel grooves of the further output drive wheel 360B, toward or away from the further output drive wheel, respectively, and are each attached to the further output drive wheel 360B in a form- or material-locking manner. The traction strand 260B is subsequently guided by means of a further guide wheel 820B toward a groove of a guide wheel 810B, which is mounted in the tool holder (not depicted) so as to be rotatable about the yaw axis G, and runs from there to a drive, as described previously in reference to the seventh design (cf. FIG. 31, for example). The traction strand 260A is guided by means of a further guide wheel 840B to a parallel groove of the guide wheel 810B, and runs from this guide wheel to the drive on the other side of the yaw axis G. The further guide wheels 820B, 830B, together with the guide wheel 810B, form a channel for guiding the traction strands 260A, 260B, in order to securely guide them on the guide wheel 810B, even in the case of yaw movements of the tool holder. The traction strand 260A forms an angle of between 15° and 75° to the yaw and pitch axes, between them.

The tool holder wheel 110' is also actuated by means of two traction strands 110A, 110B, running in opposite directions away from it. These are each attached to the tool holder wheel 110' in a form- or material-locking manner, tangentially in corresponding projections of the tool holder wheel 110', in the embodiment example of FIG. 34, of which only the upper one is visible in FIG. 34. They run from the tool holder wheel 110', away from two parallel grooves, toward two parallel grooves of a guide wheel 850, from which they run on both sides of the yaw axis G to a drive, as described above in reference to the seventh design (cf. FIG. 31, for example).

The difference to the seventh design is, in particular, that the traction strand pairs of a differential transmission run from the output drive wheel on the same side of the yaw axis, with the coil shaped tool, from the two coil flanges (above, below in FIG. 34). In that a traction strand 250B, or 250A, respectively, is guided from the output drive wheel 360A or 360B, respectively, diagonally toward the guide wheel 810A or 810B, respectively, the traction strands of a traction strand pair are guided past the yaw axis on both sides thereof, respectively. The tool holder wheel 110' is disposed centrally between the two guide wheels 810A, 810B, and the traction strands also run therefrom in the direction of the yaw axis, offset in relation to one another, toward or away from the yaw axis, respectively. This offset running, toward or away, respectively, as well as the subsequent crossing guidance, can also be provided via the guide wheel 850 in any one of the previously explained designs as well.

FIG. 35 shows the differential transmission in an angled yaw position, i.e. rotated about the yaw axis G. One sees that the traction strands 250A, 250B, 260A, or 260B, respectively, remain pressed against the guide wheel 810A or 810B, respectively, by means of the further guide wheels 820A, 820B, 830A, and 830B, even during yaw motions. At the output drive side, the traction strands 250A, 250B, 260A, or 260B, respectively, are guided in the grooves of the output drive wheels 360A, 360B by means of further guide wheels 840A, 840B. The guidance rotational axes of this further guide wheels 840A, 840B are tilted, as is the case with the guidance rotational axes of the further guide wheels 820A, 830B, toward the pitch as well as yaw axes, in order to represent the diagonal guidance of the traction strands 250B and 260A.

LIST OF REFERENCE SYMBOLS 1 shaft end
2 tool holder
3 tool (base body)
3A/3B base/further lever
30, 30A, 30B, 31C, 213, 313 drive wheel (worm wheel, crown gear)
31; 31A, 31B, 31C; 325A, 325B output drive wheel (worm wheel; crown gear wheel)
35 sliding body
36 spiral-shaped groove
37 longitudinal groove
100A, 100B, 200A, 200B, 400A, 400B, cord/belt strand
500A, 500B, ZA, ZB/100A', 100B'

100, 200; 200', 300, 317, Z traction means
100' pushing means (push bar)
110, 110' tool holder wheel
190, 210, 210', 215, 220, 290, 310, 310', intermediate wheel
315, 315', 320, 320'
250A, 250B, 260A, 260B differential transmission-traction strand
350; 350A, 350B; 350C, 350D, 360A, (additional) output drive wheel
360B
410A, 410B, 510A, 510B, 610A, 610B, (additional) guide wheel
710A, 710B, 720A, 720B, 810A, 810B,
820A, 820B, 830A, 830B, 840A, 840B,
850
A (additional) tool axis
yaw axis
N pitch axis

The invention claimed is:

1. A robot-guided surgical instrument, comprising:
a shaft end;
a tool holder, mounted on the shaft end so as to be rotatable about a yaw axis;
a tool, which includes a base lever mounted on the tool holder so as to be rotatable about a pitch axis;
a gear transmission, the gear transmission comprising an input drive wheel, which is mounted on the tool holder such that it can be rotated about an input transmission axis by a drive, and an output drive wheel contacting the input drive wheel in a force- and/or form-locking manner, the output drive wheel mounted on the tool holder so as to be rotatable about an output transmission axis, and by which, the tool can be rotated about the pitch axis; and
a further gear transmission, which has a further input drive wheel, which is mounted on the tool holder such that it can be rotated by a further drive about a further input transmission axis, and a further output drive wheel connected to the further input drive wheel in a force- and/or form-locking manner, the further output drive wheel mounted on the tool holder such that it can rotate about a further output transmission axis, and by which a further lever of the tool can be rotated about a further tool axis;
wherein the further input transmission axis is at least substantially parallel to the yaw axis and is offset from the yaw axis.

2. The surgical instrument according to claim 1, wherein the gear transmission is designed as a worm, screw, bevel, hypoid, crown, or friction gear transmission.

3. The surgical instrument according to claim 1, wherein a traction strand forms an angle with the yaw and/or the pitch axis, which is greater than 0 degrees and is less than 90 degrees.

4. The surgical instrument according to claim 3, wherein the angle is greater than 15 degrees.

5. The surgical instrument according to claim 3, wherein the angle is less than 75 degrees.

6. The surgical instrument according to claim 1, wherein a traction strand is guided by at least one guide wheel.

7. The surgical instrument according to claim 1, wherein the input and output transmission axes, and/or the pitch and the yaw axes, cross one another at least substantially at right angles, with or without an intersection; and/or the output transmission axis is, at least substantially, parallel to the pitch axis.

8. The surgical instrument according to claim 7, wherein the output transmission axis is flush to the pitch axis.

9. The surgical instrument according to claim 1, wherein the drive comprises two traction strands, a pushing means, and/or at least one intermediate wheel, by which the input drive wheel rotates about its input transmission axis.

10. The surgical instrument according to claim 1, wherein the input drive wheel is rigidly or functionally connected to the tool holder, which is rotated about the yaw axis by a drive.

11. The surgical instrument according to claim 1, wherein the tool comprises a tool base body mounted on the tool holder such that it can rotate about the pitch axis, and the base lever of the tool is rigidly connected to the tool base body or is mounted on the tool base body such that it can rotate about a tool axis.

12. The surgical instrument according to claim 11, wherein a further lever of the tool is mounted on the tool base body or the tool holder such that it can rotate about a further tool axis.

13. The surgical instrument according to claim 11, wherein the base lever of the tool is designed as an integral part of the tool base body.

14. The surgical instrument according to claim 1, further comprising a conversion transmission for converting a rotational and a translational movement to one another, and which is disposed between the output drive wheel and the lever.

15. The surgical instrument according to claim 1, wherein the base lever is a blade and/or jaw.

16. The surgical instrument according to claim 1, wherein the input transmission axis is flush to the yaw axis.

17. A robot-guided surgical instrument, comprising:
a shaft end;
a tool holder, mounted on the shaft end so as to be rotatable about a yaw axis;
a tool, which includes a base lever mounted on the tool holder so as to be rotatable about a pitch axis; and
a wraparound transmission, which includes an input drive wheel mounted on the tool holder so as to be rotatable about an input transmission axis by drive means engaging the input drive wheel, an output drive wheel mounted on the tool holder so as to be rotatable about an output transmission axis, and by which the tool can be rotated about the pitch axis, and two traction strands that are different from the drive means engaging the input drive wheel, and which couple the input and output drive wheels.

18. The surgical instrument according to claim 17, further comprising:
a further wraparound transmission, which has a further input drive wheel mounted on the tool holder such that it can rotate about a further input transmission axis by a further drive, and a further output drive wheel mounted on the tool holder such that it can rotate about a further output transmission axis, and by which a further lever of the tool can rotate about a further tool axis, and two further traction strands, differing from the further drive, which couple the further input and output drive wheels.

19. The surgical instrument according to claim 17, wherein the base lever is a blade and/or jaw.

20. The surgical instrument according to claim 17, wherein the two traction strands are interconnected.

21. A robot-guided surgical instrument, comprising:
a shaft end;

a tool holder mounted on the shaft end so as to be rotatable about a yaw axis;

a tool which includes a base lever mounted on the tool holder such that it can rotate about a pitch axis; and a differential transmission, which has an output drive wheel, mounted on the tool holder such that it can rotate about an output transmission axis, and by which the tool can rotate about the pitch axis, wherein two traction strands are offset from one another in a direction parallel to the output transmission axis, the traction strands running in opposing directions off of the output drive wheel, or onto the output drive wheel, respectively;

wherein the output transmission axis is at least substantially parallel to the pitch axis.

22. The surgical instrument according to claim 21, further comprising a further differential transmission, which has a further output drive wheel mounted on the tool holder such that it can rotate about a further output transmission axis, and by which a further lever of the tool can rotate about a further tool axis, wherein two further traction strands are offset from one another in the direction of the further output transmission axis, running in opposing directions away from the further output wheel, or toward the further output drive wheel, respectively.

23. The surgical instrument according to claim 21, wherein the base lever is a blade and/or jaw.

24. The surgical instrument according to claim 21, wherein the two traction strands are offset from one another on both sides of the yaw axis.

* * * * *

UNITED STATES PATENT AND TRADEMARK OFFICE
CERTIFICATE OF CORRECTION

PATENT NO. : 9,730,757 B2
APPLICATION NO. : 13/985466
DATED : August 15, 2017
INVENTOR(S) : Sven Brudniok It is certified that error appears in the above-identified patent and that said Letters Patent is hereby corrected as shown below:

In the Specification

Column 1, Lines 10-15, read "For some years now, minimally invasive surgical operations, in particular, in which one or more tools, disposed on distal ends of a surgical instrument are inserted in the patient, preferably by means of trocars, in which the instruments move by means of teleoperated robots controlled by the surgeon." and should read -- For some years now, minimally invasive surgical operations, in particular, in which one or more tools, disposed on distal ends of a surgical instrument, are inserted in the patient, preferably by means of trocars, in which the instruments move by means of teleoperated robots controlled by the surgeon. --.

Column 7, Line 24, reads "and a translational motions into one" and should read -- and translational motions into one --.

Column 8, Lines 11-12, read "material-locking manner, in that, for example, a lug is for flied in the traction means and is disposed in an" and should read -- material-locking manner, in that, for example, a lug is formed in the traction means and is disposed in an --.

Column 8, Lines 36-37, read "of a traction strand is connected to one end of the other traction strands, in particular" and should read -- of a traction strand is connected to one end of the other traction strand, in particular --.

Column 9, Lines 57-58, read "FIG. 19: a part of a surgical instrument according to on design of the present" and should read -- FIG. 19: a part of a surgical instrument according to one design of the present --.

Column 13, Line 63, reads "[rota-]tional and a translational motions" and should read -- -rota-]tional and translational motions --.

Signed and Sealed this
Fourth Day of September, 2018

Andrei Iancu
*Director of the United States Patent and Trademark Office*

CERTIFICATE OF CORRECTION (continued)
U.S. Pat. No. 9,730,757 B2

Column 14, Lines 56-58, read "holder 2, such that the worm 31 and the intermediate wheel 210, which is . . ., is disposed in this case between" and should read -- holder 2, such that the worm 31 and the intermediate wheel 210, which is . . ., are disposed in this case between --.

Column 17, Lines 54-55, read "on which a tool holder 2 is rotatably mounted, such that is can rotate about the" and should read -- on which a tool holder 2 is rotatably mounted, such that it can rotate about the --.

Column 22, Line 46, reads "840A, 840B. The guidance rotational axes of this further guide wheels 840A, 840B are" and should read -- 840A, 840B. The guidance rotational axes of these further guide wheels 840A, 840B are --.

In the Claims

Claim 1
Column 23, Line 33, reads "[transmis-]sion axis, and by which, the tool can be rotated about" and should read -- [transmis-]sion axis, and by which the tool can be rotated about --.